(12) United States Patent
Murphy et al.

(10) Patent No.: US 12,180,488 B2
(45) Date of Patent: Dec. 31, 2024

(54) RECOMBINATION SYSTEMS FOR HIGH-THROUGHPUT CHROMOSOMAL ENGINEERING OF BACTERIA

(71) Applicant: University of Massachusetts, Boston, MA (US)

(72) Inventors: Kenan C. Murphy, Worcester, MA (US); Christopher Sassetti, Worcester, MA (US)

(73) Assignee: University of Massachusetts, Boston, MA (US)

( * ) Notice: Subject to any disclaimer, the term of this patent is extended or adjusted under 35 U.S.C. 154(b) by 1122 days.

(21) Appl. No.: 16/960,147

(22) PCT Filed: Jan. 11, 2019

(86) PCT No.: PCT/US2019/013381
§ 371 (c)(1),
(2) Date: Jul. 6, 2020

(87) PCT Pub. No.: WO2019/140328
PCT Pub. Date: Jul. 18, 2019

(65) Prior Publication Data
US 2021/0123065 A1    Apr. 29, 2021

Related U.S. Application Data

(60) Provisional application No. 62/617,165, filed on Jan. 12, 2018.

(51) Int. Cl.
C12N 15/74    (2006.01)

(52) U.S. Cl.
CPC .................................. C12N 15/74 (2013.01)

(58) Field of Classification Search
None
See application file for complete search history.

(56) References Cited

U.S. PATENT DOCUMENTS

| | | | |
|---|---|---|---|
| 6,294,328 B1 | 9/2001 | Fleischmann et al. | |
| 2006/0046294 A1 | 3/2006 | Ow et al. | |
| 2013/0034882 A1 | 2/2013 | Chen et al. | |

FOREIGN PATENT DOCUMENTS

| | | |
|---|---|---|
| EP | 3737754 | 11/2020 |
| WO | 02077183 | 10/2002 |
| WO | 2017/075529 A1 | 5/2017 |
| WO | 2017/127612 A1 | 7/2017 |
| WO | 2019140328 | 7/2019 |

OTHER PUBLICATIONS

Nkrumah et al. Nature Methods 3, 615-621 (2006).*
"European Application Serial No. 19738889.5, Response to Communication pursuant to Rules 161(1) and 162 EPC filed Feb. 18, 2021", 9 pgs.
"European Application Serial No. 19738889.5, Extended European Search Report mailed Sep. 6, 2021", 9 pgs.
"European Application Serial No. 19738889.5, Response filed Mar. 29, 2022 to Extended European Search Report mailed Sep. 6, 2021", 10 pgs.
Marinelli, Laura J, "Recombineering : A powerful tool for modification of bacteriophage genomes", Bacteriophage 2011 Landes Bioscience USA. vol. 2 No. 1, (Jan. 22, 2012), 5-14.
Van, Kessel Julia C, "Efficient point mutagenesis in *Mycobacteria* using single-stranded DNA recombineering: characterization of antimycobacterial drug targets", Molecular Microbiology. vol. 67. No. 5, (Mar. 1, 2008), 1094-1107.
Van, Kessel Julia C, "Recombineering in *Mycobacterium tuberculosis*", Nature Methods. vol. 4. No. 2, (Feb. 1, 2007), 147-152.
PCT/US2019/013381, May 17, 2019, International Search Report and Written Opinion.
PCT/US2019/013381, Jul. 23, 2020, International Preliminary Report on Patentability.
"European Application Serial No. 19738889.5, Communication Pursuant to Article 94(3) EPC mailed Jan. 31, 2024", 5 pgs.
International Search Report and Written Opinion for Application No. PCT/US2019/013381, mailed May 17, 2019.
International Preliminary Report on Patentability for Application No. PCT/US2019/013381, mailed Jul. 23, 2020.
Genbank Accession No. CP023632.1. Sheen et al., *Mucobacterium tuberculosis* strain TBDM2189 chromosome, complete genome. Oct. 5, 2017. 1 page.
Murphy et al., ORBIT: a New Paradigm for Genetic Engineering of Mycobacterial Chromosomes. mBio. Dec. 11, 2018;9(6):e01467-18. doi: 10.1128/mBio.01467-18. 20 pages.

* cited by examiner

*Primary Examiner* — Oluwatosin A Ogunbiyi
(74) *Attorney, Agent, or Firm* — Schwegman Lundberg & Woessner, P.A.

(57) ABSTRACT

In some aspects, the disclosure relates methods and compositions for genetic engineering of cells (e.g., bacterial cells, etc.). The disclosure is based, in part, on a combination of genetic recombination systems (e.g., a "targeting oligonucleotide" and a "payload plasmid) that enable high-throughput chromosomal engineering and do not involve the preparation of double-stranded DNA (dsDNA) recombination substrates. In some aspects, the disclosure provides engineered bacterial cells comprising a targeting oligonucleotide and a payload plasmid.

19 Claims, 11 Drawing Sheets
Specification includes a Sequence Listing.

| Target | # correct/ # tested |
|---|---|
| MSMEG_2379 (leuB) | 2/4 |
| MSMEG_4217 (DivIVA) | 3/4 |
| MSMEG_2723 (recA) | 4/4 |
FIG. 2C
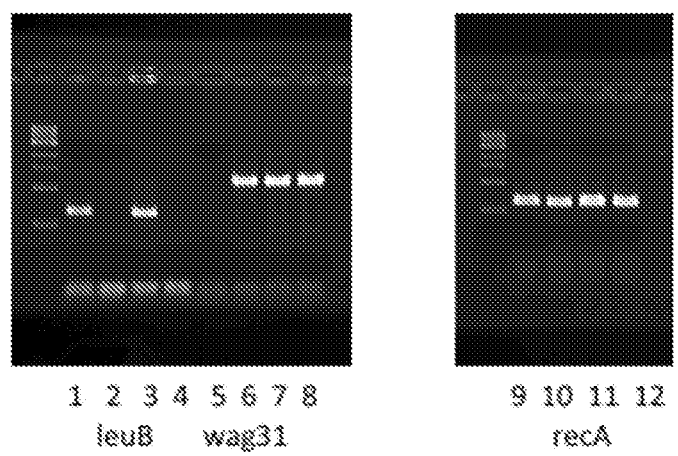
FIG. 2D
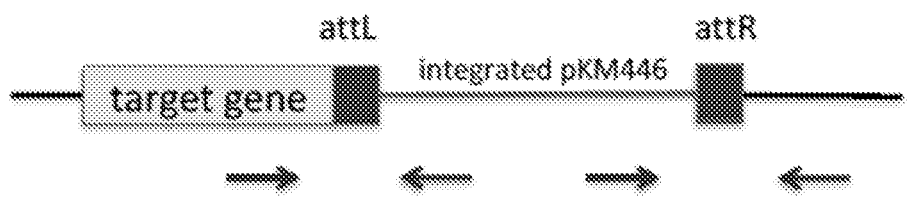
FIG. 2E Bxb1 *attP* sequence

GGTTTGTCTGGTCAACCACCGCGGTCTCAGTGGTGTACGGTACAAACC (SEQ ID NO: 79)

SEQUENCE LISTING

<160> NUMBER OF SEQ ID NOS: 81

<210> SEQ ID NO 1
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 1
cctggtatct ttatagtcct gtcg                     24

<210> SEQ ID NO 2
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 2
tgcacgggac caacaccttc gtgg                     24

<210> SEQ ID NO 3
<211> LENGTH: 24
<212> TYPE: DNA
<213> ORGANISM: Artificial Sequence
<220> FEATURE:
<223> OTHER INFORMATION: Synthetic polynucleotide

```
<400> SEQUENCE: 3
gaggaactgg cgcagttcct ctgg                                          24

<210> SEQ ID NO 4
<211> LENGTH: 191
<212> TYPE: DNA
<213> ORGANISM: Artificial Sequence
<220> FEATURE:
<223> OTHER INFORMATION: Synthetic polynucleotide

<400> SEQUENCE: 4
gacgttcttg gcctgctcct cacgggtgcg aggatcctgc gcctgctcgc cgtcggggac    60
gtccgacggc tcaggtttgt accgtacacc actgagaccg cggtggttga ccagacaaac   120
cgaagtcaac cggggccggg aggacgtcat cggcttcagc ggtcacgacg gcgccgatac   180
cgagcttctc t                                                       191

<210> SEQ ID NO 5
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 5
cagtggccga cacagcactg agtggcgcac aggccggaaa gcctgtgcgc cttcgacgcg    60
aaaactccta ggtttgtacc gtacaccact gagaccgcgg tggttgacca gacaaaccga   120
gcagagaacg gatccgctcg cccaccgcgc tggtggacag cttctcgtcg ccgcgggtgg   180
ccagatgc                                                           188

<210> SEQ ID NO 6
<211> LENGTH: 191
<212> TYPE: DNA
<213> ORGANISM: Artificial Sequence
<220> FEATURE:
<223> OTHER INFORMATION: Synthetic polynucleotide

<400> SEQUENCE: 6
tccgaccacg gtgacggacc catcgagtca gccccgggtc gtgtcgacgc ggggcctgtc    60
gccggacgag tcaggtttgt accgtacacc actgagaccg cggtggttga ccagacaaac   120
cgttgttgcc gcggttgaac tggccgaatc cgctggcgtc gctgttcgcg ctggaatcga   180
ccggtgcggc c                                                       191

<210> SEQ ID NO 7
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 7
agagaagctc ggtatcggcg ccgtcgtgac cgctgaagcc gatgacgtcc tcccggcccc    60
ggttgacttc                                                          70

<210> SEQ ID NO 8
<211> LENGTH: 45
<212> TYPE: DNA
<213> ORGANISM: Artificial Sequence
<220> FEATURE:
<223> OTHER INFORMATION: Synthetic polynucleotide
```

```
<400> SEQUENCE: 8
ggtttgtctg gtcaaccacc gcggtctccg tcgtcaggat catcg          45

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9
gactacaagg acgacgacga caag                                 24

<210> SEQ ID NO 10
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 10
gccgccaacg acgagaacta ctccgagaac tacgcggacg ccagctag       48

<210> SEQ ID NO 11
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 11
agaaaggagg aagga                                           15

<210> SEQ ID NO 12
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 12
gggcgccgct tgctggactt ggccatgagt gtctatcttt ccgtttcttg atttgcagtt    60
cttggggtca ggtttgtacc gtacaccact gagaccgcgg tggttgacca gacaaaccga   120
atggcggttc gtcatcgccg ccgccgaacg aacccgacgc cggtgcgctg ccccacgggt   180
catctccc                                                           188

<210> SEQ ID NO 13
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 13
catcgccagc aggtgcaatg gacctgaccc gtaggagttt ttgaaacgcg ttgcaatgtc    60
gaacatttca ggtttgtacc gtacaccact gagaccgcgg tggttgacca gacaaacccc   120
tcttgtggaa ttcgatgcca gcgacccatt tcgtgttgtg cacaccgggc agtgcgggaa   180
cgatgatg                                                           188

<210> SEQ ID NO 14
```

<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 14
aggtggcact ctcaacgagg aggatcggca gtgagccact accggagcaa cgtccgtgac    60
ggtttgtctg gtcaaccacc gcggtctcag tggtgtacgg tacaaaccat catggaactc   120
gacgaggccg cgttctgatc cttatctgtt gactctgcgt ccaccgga                168

<210> SEQ ID NO 15
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 15
ccacacccgc atactcgcgc tgtacgtcat ttagcctctc cgtcctggat gctcggccag    60
ctcttcgtcg ggtttgtacc gtacaccact gagaccgcgg tggttgacca gacaaaccac   120
tacgtcgtag gagtgccgct cgacctcaac cataaaacct cgctcagctt ctgaaacgat   180
ccttcagc                                                            188

<210> SEQ ID NO 16
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 16
accataaaac ctcgctcagc ttctgaaacg atccttcagc caataaatct gagatctgtg    60
atgctgccac ggtttgtacc gtacaccact gagaccgcgg tggttgacca gacaaacccc   120
gatcgcagga cggttcgccg tgggtgcgct catctaatgt gatcctcttc gcgtgttatc   180
tcgtcgaa                                                            188

<210> SEQ ID NO 17
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 17
gtcttcacaa cacccggtac gctcggttgg gtgtccaaga cctacgtcgg ctcgcgggtc    60
ggtttgtctg gtcaaccacc gcggtctcag tggtgtacgg tacaaaccgt gtccccgtat   120
ctggtgaaac aactatgacc ggtcagaacg gccaagtcgc gcgtatct                168

<210> SEQ ID NO 18
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 18
cgatctagtg gggaaagtag ggtccgttca atgacgtcac agggcgacac gacaagcggc    60
ggtttgtctg gtcaaccacc gcggtctcag tggtgtacgg tacaaaccga cgtctgccag   120
ttcactctgg tcaaataagg gtcagccgaa aaagatgttg cgacggcc    168

```
<210> SEQ ID NO 19
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 19
```
acacacactg tcagcgccgg ctgtcgaaat ggttgcgtag cggcatacgg cgtgcgaact    60
ctgctgctca ggtttgtacc gtacaccact gagaccgcgg tggttgacca gacaaaccgc    120
ccgttgcaga cgccgaattt tcacgacgtt ccaaccgctt gtccagcacc gctagcacga    180
ccagcgcg    188

```
<210> SEQ ID NO 20
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 20
```
ttgtacggtt ggcgcgggag gttgtcgcct atggccaagc tgagaccata ttacgaagag    60
ggtttgtctg gtcaaccacc gcggtctcag tggtgtacgg tacaaaccaa cgtcgcccag    120
ttcaccatga ccaagtagct cgtccgctca tatccgttcc ctgacctg    168

```
<210> SEQ ID NO 21
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 21
```
ctggcgagca gacgcaaaag cccctaatac ctgccggttt aggggctttt gcgtctgct    60 cgccggccta ggtttgtacc gtacaccact gagaccgcgg tggttgacca gacaaacccc    120
gcgcgtctat ggtgacgtag tcgcgctccg tgtagccggt gtagatctgg cggggccggc    180
cgatcttg    188

```
<210> SEQ ID NO 22
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 22
```
tttaccggct ggtcgagcgc ctcgatgctc attgagggac tcacccgttg accttcccgc    60
cggcgattgc ggtttgtacc gtacaccact gagaccgcgg tggttgacca gacaaaccta    120
cggcggcacc aaatcggttg agtttcaatt cagttcctaa cggccgacca gctgttttgc    180
tcgcagca    188

```
<210> SEQ ID NO 23
<211> LENGTH: 188
<212> TYPE: DNA
<213> ORGANISM: Artificial Sequence
<220> FEATURE:
```

<223> OTHER INFORMATION: Synthetic polynucleotide

<400> SEQUENCE: 23

| | | |
|---|---|---|
| tttaccggct ggtcgagcgc ctcgatgctc attgagggac tcacccgttg accttcccgc | 60 |
| cggcgattgc ggtttgtacc gtacaccact gagaccgcgg tggttgacca gacaaaccta | 120 |
| cggcggcacc aaatcggttg agtttcaatt cagttcctaa cggccgacca gctgttttgc | 180 |
| tcgcagca | 188 |

<210> SEQ ID NO 24
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 24

| | | |
|---|---|---|
| gtgtcaatgt tgtgcgcatg cctacggcca cgagcatgat cccggcagtc agcctgggtg | 60 |
| acccgcaatt ggtttgtctg gtcaaccacc gcggtctcag tggtgtacgg tacaaaccca | 120 |
| ttgatcgacc acgcgatatc tgcgtgcgac tagcgacaca ccccagcaac tacctgttga | 180 |
| cacaacga | 188 |

<210> SEQ ID NO 25
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 25

| | | |
|---|---|---|
| ctttccgtcg agccatgggg ccgggcatcc cccaccccgg aaccgtccgt gccgtatcgt | 60 |
| cgccaggcta ggtttgtacc gtacaccact gagaccgcgg tggttgacca gacaaaccct | 120 |
| gctctgtcag acccagtcgc gccaccaacc atcgccgcaa gtccgggccg tagtcgtcac | 180 |
| gatccaat | 188 |

<210> SEQ ID NO 26
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 26

| | | |
|---|---|---|
| tcgggcgccg ccgtgtcgcg cggtgatcgg cgctctcgcg cttatgcgcg ccaacgacag | 60 |
| gcccgcgtca ggtttgtacc gtacaccact gagaccgcgg tggttgacca gacaaaccgc | 120 |
| ggccgaccag actccactcc tcgagcccgt cgtagagcgg aaacgccctg ccagccggg | 180 |
| tcgcccga | 188 |

<210> SEQ ID NO 27
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 27

| | | |
|---|---|---|
| ggtgcaatag tttggggaag ggtgtccataa atgaggctgt cgttgaccgc attgagcgcc | 60 |
| ggtttgtctg gtcaaccacc gcggtctcag tggtgtacgg tacaaacctc ggttgccggc | 120 | tcctgcaaca actattaagc ccatgcgggc cccatcccgc gacccggc                  168

<210> SEQ ID NO 28
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 28
tcacgcacgc gattctcgat gcagaggcag atgaagcgag tgattgcggg agcattcgcg     60
ggtttgtctg gtcaaccacc gcggtctcag tggtgtacgg tacaaacctt actgggctcc   120
cccgccttcg gcggctaaac actaccgctt tgatccgtct gccacggc                168

<210> SEQ ID NO 29
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 29
cgctcgagtc cgccctgggc ggctctttcc ttgggcaggg tcatccgacg tgtttccgcc     60
gtggtttgcc ggtttgtacc gtacaccact gagaccgcgg tggttgacca gacaaacccg   120
ccgcaggcga atattccggg aaggccatca ggccgtcaag tttagtggtg acccggccac   180
gcctaccg                                                            188

<210> SEQ ID NO 30
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 30
gcagcatgcg cagtgtgcga cagttaccca atgctcctgg ccctgctgcg ccagcacatc     60
ggtttgtctg gtcaaccacc gcggtctcag tggtgtacgg tacaaaccct gagcgccacg   120
gtcgggggtg tagggtgacc gcgccaccgg gcgcacgccc ccgtgccg                168

<210> SEQ ID NO 31
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 31
tttgcggcgc cgagccatcg catcagttta atcgcgcaac tcagaacagc cggtactcgc     60
cgctatccat ggtttgtacc gtacaccact gagaccgcgg tggttgacca gacaaaccct   120
gggcgatgac tagacgcacc cgactcacct tagagcgcgc aacgacgttg ttccttagag   180
cgtgaccg                                                            188

<210> SEQ ID NO 32
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 32
agcagacgca gaatcgcacg cggaagcctt tccgcgtgcg attctgcgtc tgctcgcgcc      60
ctcgacgcta ggtttgtacc gtacaccact gagaccgcgg tggttgacca gacaaaccga     120
tggcgcgctt gaggtcgtcg accttgtcga gctgctccca cggtaattcg acgtcggtgc     180
ggccgaag                                                              188

<210> SEQ ID NO 33
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 33
cggtgaggcg gactactacc gcaacggcgg catcctgcag tacgtgctgc gcaacatact      60
gaagtcaggc ggtttgtctg gtcaaccacc gcggtctcag tggtgtacgg tacaaacctg     120
accgagcgcc cgtgcccaag gtcagcgagg accatctggc ggctcgccgc cgtcagatcc     180
tcgacggt                                                              188

<210> SEQ ID NO 34
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 34
cggtgaggtc aaaccactca tcggaccact ctattgagtc aacctggggg gcgtccccag      60
ggtttgtacc gtacaccact gagaccgcgg tggttgacca gacaaaccaa acaccagacc     120
agcaacggct ccttgcaccg gaattccttt ctcgagtccc tacacgtc                  168

<210> SEQ ID NO 35
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 35
tgattgttcg gtttcggaag gctcatggtg tcaccaatgg atccctcggg tggcccgcac      60
ggtttgtacc gtacaccact gagaccgcgg tggttgacca gacaaaccga cgaagttcgt     120
taagtcacca agattcatcg tgggtagctc ctgatggcgg cgtggggt                  168

<210> SEQ ID NO 36
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 36
atcacgcgcg aggatgccgg atggccatga agggagccta atggtagagc ccggcaattt      60
ggcaggcgcg ggtttgtctg gtcaaccacc gcggtctcag tggtgtacgg tacaaaccgg     120
caggaagttg agccgccgtc cgctctgacc tggccaatgc gctctgcgca taccggcgcg     180
aactcgga                                                              188

```
<210> SEQ ID NO 37
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 37
tcggccccgt agtatctccg gagatgacag atgaatgtcg tcgacatttc gcggtggcag      60
ggtttgtctg gtcaaccacc gcggtctcag tggtgtacgg tacaaaccaa caacaccaac     120
gccagcgcaa agacctgagt catcgatatc agcacgtaac gccgctca                  168

<210> SEQ ID NO 38
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 38
gcggcgctgc gccgctatct actcagcacg gtggcctgcg gggtcgggat ctccggctgc      60
ggtttgtctg gtcaaccacc gcggtctcag tggtgtacgg tacaaaccga agtgaactcg     120
gatggtttcc gacgatgaac cgaccgagtg ctgtgagtcg ccgccagc                  168

<210> SEQ ID NO 39
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 39
tcggccccgt agtatctccg gagatgacag atgaatgtcg tcgacatttc gcggtggcag      60
ggtttgtctg gtcaaccacc gcggtctcag tggtgtacgg tacaaaccga ggtagcacca    120
ttgtcgtttg cttactgagg ccaactgacc ccggaaagga gcagccgg                  168

<210> SEQ ID NO 40
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 40
cgcgcaccgc tgcggacatg ctgcgagagc aagcggaatt gtccgggacg aggccacacc      60
acccgcgcta ggtttgtacc gtacaccact gagaccgcgg tggttgacca gacaaacccc    120
cgatcagcct cgcgagccag ctcggatcct gatagttcac gaccatgctg ccgtcccaca    180
cgaacggc                                                              188

<210> SEQ ID NO 41
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 41
ttccacctgg gttgggcagt gaactgccgc ctagcacgcc ttgaggcgaa tcttccagcg      60
ggtttgtacc gtacaccact gagaccgcgg tggttgacca gacaaaccgg gcggggcggc    120
```
tggttggctc atcggcacca actgtatcgg gaccgcagcc gacgccgg        168

<210> SEQ ID NO 42
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 42
acggtcctac gttagttcat gcgtaggctc atggcggtga gcgcacgtgc gggcatcgtg        60
ggtttgtctg gtcaaccacc gcggtctcag tggtgtacgg tacaaaccac cctgagcggt       120
atcccgggct caccctagcg acggcgaaat cgacagcagc gcgacaaa                    168

<210> SEQ ID NO 43
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 43
cccgtcacaa gctgacacga cgaactaggt tcagcgactg agatcgcttc ccggaagcgc        60
ggtttgtacc gtacaccact gagaccgcgg tggttgacca gacaaacctc cgctggcccc      120
ggtgacggcg attctcacgg tcctactcgt cgtcgttccg aaacgccg                    168

<210> SEQ ID NO 44
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 44
ggctgaagtg tcttgcggtg atgagccgag cagttctcga cgcatatagc cggccagcgc        60
ggtttgtacc gtacaccact gagaccgcgg tggttgacca gacaaacccc cggccagatc      120
ccacccacgg tcggtgggaa attctgacat cacgtccctg cgtcggc                     168

<210> SEQ ID NO 45
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 45
cgcccgccag taccggatcg acgacgtggc ggctgcgccc gagcagacca cggatcccgg        60
tcccggggcc ggtttgtctg gtcaaccacc gcggtctcag tggtgtacgg tacaaaccta      120
acgccggcga gccgaccgcc tttggccgaa tcttccagaa atctggcgta gcttttagga      180
gtgaacga                                                                188

<210> SEQ ID NO 46
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 46
agcccgacga tgacgaccgg gtcgttatcg acatcggca ctcaccatcc gggccacggc        60

```
gtcgaggtga ggtttgtacc gtacaccact gagaccgcgg tggttgacca gacaaacccg    120
aatgatctcc gagcacgccg tagcatgcac cacaaaccct ccctgttag cacaggctgc     180 cctaattt                                                              188
```

<210> SEQ ID NO 47
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 47

```
acctgcgcta ccagccccc tgttaaggag cccacatgcc accgaaggcg gcagatggcc     60
gccgacccag ggtttgtctg gtcaaccacc gcggtctcag tggtgtacgg tacaaacccg    120
acgggtcccg tgacgaccca gcgctgccat tgactgacgt caacaagttg aattgactgc    180
gttgcatg                                                              188
```

<210> SEQ ID NO 48
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 48

```
gaagtcgccg tagcgtttgg tggcgtcggc cacgacgatg gcgtaggtca ttttcaccgt    60
ctccttctca ggtttgtacc gtacaccact gagaccgcgg tggttgacca gacaaaccgc    120
cctcgctgac cgctcgtgcc cggcgggcgt ctagcaccat ctggacgatc agcaccacca    180
cggaaacc                                                              188
```

<210> SEQ ID NO 49
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 49

```
tcatttgatt gggtccacgg aagcaggtag cttccgtcgc atgcttttg cggctttgcg     60 tgatgtccaa ggtttgtctg gtcaaccacc gcggtctcag tggtgtacgg tacaaaccat    120
tgagcaccgc gagcttgcca gcgaatagtt cggcaccaag tcgcgatccc tgagggttgc    180
gatgggcg                                                              188
```

<210> SEQ ID NO 50
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 50

```
tcatttgatt gggtccacgg aagcaggtag cttccgtcgc atgcttttg cggctttgcg     60 tgatgtccaa ggtttgtctg gtcaaccacc gcggtctcag tggtgtacgg tacaaaccat    120
tgagcaccgc gagcttgcca gcgaatagtt cggcaccaag tcgcgatccc tgagggttgc    180
gatgggcg                                                              188
```

<210> SEQ ID NO 51
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 51
tgcttgctgc ggcactgaag acttgacctc gtgagcgtcg tcgcggtcac catcttcgtg    60
ggtttgtctg gtcaaccacc gcggtctcag tggtgtacgg tacaaacctg gttgcggtac   120
ttcgtgttgt tgcactgacc atctgtattg ccgacagacc tgtagcac                168

<210> SEQ ID NO 52
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 52
aaactccttg tccacctcgc aatcgtcatc aggtgaacgc cgccggcggt ggggttggtt    60
cccgcaatca ggtttgtacc gtacaccact gagaccgcgg tggttgacca gacaaaccgc   120
tggcggtctg gcggatcccc ccgatgtccc gcagagccct ggccacgtaa tcgacaccag   180
tgatcacg                                                            188

<210> SEQ ID NO 53
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 53
cggagccgac atctgcgaac tcccttggt gggaactgac ggccactgaa tgaaaagctg     60 accccctatca ggtttgtacc gtacaccact gagaccgcgg tggttgacca gacaaaccgc  120
ttacggtcac aataggcgaa ccgctcggtg tcgcgcccgg atcttgctcg cccatttcgg   180
cggccagc                                                            188

<210> SEQ ID NO 54
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 54
cgctcgacga gctcactcaa cggccgtgcg gtcactgcat cccttttcgcg tacagacggt   60 caccgcgtca ggtttgtacc gtacaccact gagaccgcgg tggttgacca gacaaacccc  120
ctagcgaacc ttgattgtct ggctccccaa acgattgcca gcccgcgtat ccagtccact   180
cctcgccg                                                            188

<210> SEQ ID NO 55
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 55

```
gcgggcctaa cacacggata cccttcgtca cattgccacc gtgcaaaggg tatccgtgtg    60
tcttgaccta ggtttgtacc gtacaccact gagaccgcgg tggttgacca gacaaacctt   120
tgcgaccccg ccgagcggtt gccttcttgg cgggagcctt ggtagccggc cgcttggccg   180
ctgccttc                                                            188
```

<210> SEQ ID NO 56
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 56

```
ggcagccaat ttcgcgtacc cgatgtggat ggtcgccgga gcaccatcgg ctttagggtg    60
ctcggggcta ggtttgtacc gtacaccact gagaccgcgg tggttgacca gacaaaccgc   120
gggccgcctt cttgcgttcg atgtcggcca aggcagcggc tagctcagcg cgctgcgcgg   180
ccgatgcc                                                            188
```

<210> SEQ ID NO 57
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 57

```
atccgcacaa atgtaaggag ctgagacaca atggatttcg cactgttacc accggaagtc    60
ggtttgtctg gtcaaccacc gcggtctcag tggtgtacgg tacaaaccgt gatggcccac   120
ccacccgcgg cagggtaacc cggcgcctaa ccgacaggcg gcccgttg                168
```

<210> SEQ ID NO 58
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 58

```
ggcggctcga cattcacacc ggtcagccta gtagagccca tcggggtgta ttgggcctgt    60
atcggtccta ggtttgtacc gtacaccact gagaccgcgg tggttgacca gacaaaccgt   120
acatcaccat gtcgggctgc atctgcttgg cccacgcgac gatcccaccc tgcaggtgta   180
ccgcgtcg                                                            188
```

<210> SEQ ID NO 59
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 59

```
acacgaccga caccgtcacc gaaaggccgc ttaccctcgt atgaccgcag tgaaacacac    60
aactgaatca ggtttgtctg gtcaaccacc gcggtctcag tggtgtacgg tacaaaccca   120
ggacggcttc gccgcgcggg ctaactgacc cgcccaccgc atggttaaac cggagcgccg   180
caccaaga                                                            188
```

<210> SEQ ID NO 60
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 60
agcagtgatc ccggcagttt ctggatccag ggtcattgag caacgtggcg acacactagt    60
cgctctgggt ggtttgtctg gtcaaccacc gcggtctcag tggtgtacgg tacaaacctg   120
atcgcctatg ttggcgcgag cagacgcaaa atcgcccgaa accgatggct ttcgggcgat   180
tttgcgtc                                                            188

<210> SEQ ID NO 61
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 61
atcagcgacc tgcacgacca cgaccactga gcgcctcgcc atgaccctgg aagtggtatc    60
ggacgcggcc ggtttgtctg gtcaaccacc gcggtctcag tggtgtacgg tacaaacccg   120
gttgatccgc taccgcctgg accgctagca gccgcagccg tgaccacgcc aggtgcggat   180
gccctgcc                                                            188

<210> SEQ ID NO 62
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 62
cttcggactg ggccaggtcg ccagcggtag gctcgatgat gtgccgcttc ccgcagaccc    60
tagccccacc ggtttgtctg gtcaaccacc gcggtctcag tggtgtacgg tacaaaccga   120
agaaccagga gtggtacccg tcgtatgacc gcgcccgcga gcctgcccgc gccgctagca   180
gaggtggt                                                            188

<210> SEQ ID NO 63
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 63
gtaggcggtt tttgtcggtg cctgttggca cgatggctag gtgaggttcg cgcagccttc    60
agcactgagc ggtttgtctg gtcaaccacc gcggtctcag tggtgtacgg tacaaacccg   120
cacacctcgc ggtctgcggc ggcggtaagc catgcccgag ggcgacaccg tctggcacac   180
cgcggcca                                                            188

<210> SEQ ID NO 64
<211> LENGTH: 188
<212> TYPE: DNA
<213> ORGANISM: Artificial Sequence
<220> FEATURE:
<223> OTHER INFORMATION: Synthetic polynucleotide

```
<400> SEQUENCE: 64
gccagagtga aatccacgac gcgtttgcgg cgtgtcgcgt cgcccgtttc actgtcggcg      60
cagaggttca ggtttgtacc gtacaccact gagaccgcgg tggttgacca gacaaacccc     120
ggaagtcgcg cgagcgcgcg ccgaccgcca gggtgaggcg gcccatccgt tcggcgacga     180
cggtgatt                                                              188

<210> SEQ ID NO 65
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 65
atccggcttc atcgctgcag tatgaccccc tttacatcgg gccagttaat cagtctctca      60
ggtggcgtca ggtttgtacc gtacaccact gagaccgcgg tggttgacca gacaaaccgc     120
ccccaacggt caggccgacc ttctggaact ccttgaggtc gcaatacccg gccttggcca     180
tcgatcgg                                                              188

<210> SEQ ID NO 66
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 66
tttacgctat cgggtctcat gcctattcgg acgccccgcg ccgcgtcggg gttccagcat      60
ttccggttca ggtttgtacc gtacaccact gagaccgcgg tggttgacca gacaaaccgc     120
gcgcggtgct caccgcgtcg gcgaccgtgg ccgccagccg ctgggcgacg ccctcgtcgg     180
ctgcctcc                                                              188

<210> SEQ ID NO 67
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 67
tgtgcgcgcg tctggcctgc tgcccaggtg ggaacagacg cagcggttca ttggggagat      60
gcgcggcacc ggtttgtctg gtcaaccacc gcggtctcag tggtgtacgg tacaaaccta     120
gctcggtaat cccttgtgtt gctttagctt cagcggtcac agcgcggcga ttgttgtcgg     180
tggcccct                                                              188

<210> SEQ ID NO 68
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 68
ccgtatctcg gcttgcagct ggcgctgctc cggcgtcagg tcaatgaaca tcgcgctccc      60
aggagctcaa ggtttgtacc gtacaccact gagaccgcgg tggttgacca gacaaaccac     120
```

```
ggcttgctgt tccgcagtgg gatcgaaatc cattagtgag caaccgggca tctaccggtg    180
tagtcgac                                                              188
```

<210> SEQ ID NO 69
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 69

```
gcgctcccga cgcaccacct cgcgcggtca tgaaagtggc ggtacttgcc gagtccgagc    60
tcggatcgga ggtttgtctg gtcaaccacc gcggtctcag tggtgtacgg tacaaacctg   120
cggctgctga tcggcgatca agacagcgcc tagaagactt acgccggcgg acccgcggtg   180
cggccccg                                                              188
```

<210> SEQ ID NO 70
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 70

```
cacgacgtgc cagcttacct gcccaattgc tgcaacctgc ggcgcgcgcg tccggaccag    60
gagtgcgcta ggtttgtacc gtacaccact gagaccgcgg tggttgacca gacaaacccc   120
gcaacgaaac caccaatgcc gtagcgattg cggccaagcc ctcgccgcgg ccagtgaggc   180
ccagcccg                                                              188
```

<210> SEQ ID NO 71
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 71

```
tcgcgcaccc ggtcgctggc cgcagcaacg cccgggagct ccattagcgg agccagcggg    60
tcgaccgtca ggtttgtacc gtacaccact gagaccgcgg tggttgacca gacaaaccca   120
ggttgccaac ctttcgggga gctgaggggg caccgggaat ggcctgaagc aactggcggg   180
tgtactcg                                                              188
```

<210> SEQ ID NO 72
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 72

```
ctcggaatca cttgcccagc aggggttcg atgagtgtca caccgaagac cctcgatatg     60
ggtttgtctg gtcaaccacc gcggtctcag tggtgtacgg tacaaaccaa cgatgcgggc   120
cgcgcagcgg gccgctgagg aaccggccca tcagtgacgg tcggcaac                 168
```

<210> SEQ ID NO 73
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 73

```
cgagcgtgcg gacatgttca ggcgcacagc gaaagctagg acacgtcaac ccaatccagg      60
gtccgctgca ggtttgtacc gtacaccact gagaccgcgg tggttgacca gacaaacctc     120
ggccaattgc tctcctagga tggcgtcgga cactgcatgt aatcgtccat gatggtccac     180
cgcagcgg                                                              188
```

<210> SEQ ID NO 74
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 74

```
cggcgggctt gcctaacgca gagctctcac atgaaatgtc caggcgtctc cgactgcgtt      60
ggtttgtctg gtcaaccacc gcggtctcag tggtgtacgg tacaaaccgg tttgctaccc     120
aaagggaaga agcactagcc ataaagtcca cgacctacgg tggcgttt                  168
```

<210> SEQ ID NO 75
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 75

```
cgtcgacaac gcgtcgaaag gtcgcctgcc atgctcgccg ccacactgct aagtctggga      60
ggtttgtctg gtcaaccacc gcggtctcag tggtgtacgg tacaaaccgg ccgcatccgc     120
ccgacacggt catcctgatc tgctcgccga acacgtgggc gacggacc                  168
```

<210> SEQ ID NO 76
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 76

```
cgccgcggtg cacgcacacc tcaacatgag agaatgaact atggggcttc gcctcaccac      60
caaggttcag ggtttgtctg gtcaaccacc gcggtctcag tggtgtacgg tacaaaccgt     120
tcccgccgga gcctccggag cccctgatg acgaccaaga agttcactcc caccattacc     180
cgtggccc                                                              188
```

<210> SEQ ID NO 77
<211> LENGTH: 188
<212> TYPE: DNA
<213> ORGANISM: Artificial Sequence
<220> FEATURE:
<223> OTHER INFORMATION: Synthetic polynucleotide

<400> SEQUENCE: 77

```
cacggccgga cagtaaccaa tcggtggcgg catagcactt caccctggct ggccgtgccc      60
ggcccggtca ggtttgtacc gtacaccact gagaccgcgg tggttgacca gacaaaccgg     120
acgcggcgta atcgtgatc tccgagatgt cggcttgact ctttccgtcg gtggttccca     180
```

```
aggtagag                                                                  188
```

<210> SEQ ID NO 78
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 78

```
gaatggcacg acggtgattg tggcagagaa ctaccaccca cgacgacgcg gcgcggaacc    60
ggtttgtacc gtacaccact gagaccgcgg tggttgacca gacaaaccgg tccaccgacg   120
tgaggtgtaa cggtcacggg atgaccctcc tcgtcatgag cggtgtgg              168
```

<210> SEQ ID NO 79
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 79

```
ggtttgtctg gtcaaccacc gcggtctcag tggtgtacgg tacaaacc                 48
```

<210> SEQ ID NO 80
<211> LENGTH: 329
<212> TYPE: PRT
<213> ORGANISM: Mycobacteriophage Phayonce

<400> SEQUENCE: 80

```
Met Thr Ser Thr Glu Val Ala Lys Asn Thr Asp Ala Glu Pro Thr Leu
1               5                   10                  15

Pro Gln Leu Ile Gln Gln Met Lys Pro Glu Ile Ala Lys Ala Leu Pro
            20                  25                  30

Ala Gln Met Asn Pro Glu Arg Met Ala Arg Ile Ala Thr Thr Val Leu
        35                  40                  45

Lys Gln Thr Pro Ala Leu Ala Arg Cys Thr Pro Ala Ser Phe Leu Gly
    50                  55                  60

Ala Leu Met Thr Ala Ser Gln Leu Gly Leu Glu Pro Gly Pro Leu Gly
65                  70                  75                  80

Glu Ser Tyr Phe Val Pro Tyr Gly Lys Asp Val Thr Phe Ile Pro Gly
                85                  90                  95

Tyr Arg Gly Leu Ile Lys Leu Ala Arg Asn Ser Gly Leu Leu Val Asp
            100                 105                 110

Ile Trp Ala Glu Ile Val Tyr Ala Asn Asp Glu Phe Lys Tyr Thr Leu
        115                 120                 125

Gly Leu His Arg Asp Leu Gln His Val Pro Ala Thr Gly Asp Arg Gly
    130                 135                 140

Lys Pro Ile Tyr Val Tyr Ala Ala Ala Lys Leu Lys Asp Gly Gly Thr
145                 150                 155                 160

Pro Phe Val Val Met Thr His Ala Glu Val Glu Ala Ile Arg Ala Arg
                165                 170                 175

Ser Arg Ala Gly Lys Asn Gly Pro Trp Val Thr Asp Trp Asn Ala Met
            180                 185                 190

Ala Lys Lys Thr Ala Val Lys Gln Leu Ala Lys Trp Leu Pro Leu Ser
        195                 200                 205

Ala Glu Phe Asn Thr Ala Thr Val Met Asp Gly Thr Val Arg Ser Asp
    210                 215                 220
```

-continued

Tyr Thr Ser Asn Leu Ile Asp Val Lys Pro Glu Tyr Ile Asp Gly Glu
225                 230                 235                 240

Val Asp Asp Asn Ala Thr Asp Pro Glu Pro Ala Glu Met Val Pro Asp
            245                 250                 255

Thr Asp Pro Asn Val Ile Asp Gly Glu Ala Thr Glu Ile Arg Met Ala
        260                 265                 270

Ser Lys Asp Gln Leu Lys Arg Leu Ser Glu Ile Gln Arg Ala Glu Lys
    275                 280                 285

Tyr Thr Asp Glu Asp Trp Phe Thr Phe Leu Ala Glu Ala Ala Gly Val
290                 295                 300

Gln Ala Thr Arg Ala Gly Glu Leu Thr Phe Glu Glu Ala Thr Arg Ala
305                 310                 315                 320

Ile Ala Val Phe Asp Gly Pro Asp Leu
                325

<210> SEQ ID NO 81
<211> LENGTH: 500
<212> TYPE: PRT
<213> ORGANISM: Mycobacteriophage Bxb1

<400> SEQUENCE: 81

Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Arg Pro Asn Leu Ala Arg Trp
    50                  55                  60

Leu Ala Phe Glu Glu Gln Pro Phe Asp Val Ile Val Ala Tyr Arg Val
65                  70                  75                  80

Asp Arg Leu Thr Arg Ser Ile Arg His Leu Gln Gln Leu Val His Trp
                85                  90                  95

Ala Glu Asp His Lys Lys Leu Val Val Ser Ala Thr Glu Ala His Phe
            100                 105                 110

Asp Thr Thr Thr Pro Phe Ala Ala Val Val Ile Ala Leu Met Gly Thr
        115                 120                 125

Val Ala Gln Met Glu Leu Glu Ala Ile Lys Glu Arg Asn Arg Ser Ala
    130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Glu Trp Arg Leu Val Pro
                165                 170                 175

Asp Pro Val Gln Arg Glu Arg Ile Leu Glu Val Tyr His Arg Val Val
            180                 185                 190

Asp Asn His Glu Pro Leu His Leu Val Ala His Asp Leu Asn Arg Arg
        195                 200                 205

Gly Val Leu Ser Pro Lys Asp Tyr Phe Ala Gln Leu Gln Gly Arg Glu
    210                 215                 220

Pro Gln Gly Arg Glu Trp Ser Ala Thr Ala Leu Lys Arg Ser Met Ile
225                 230                 235                 240

Ser Glu Ala Met Leu Gly Tyr Ala Thr Leu Asn Gly Lys Thr Val Arg
                245                 250                 255

Asp Asp Asp Gly Ala Pro Leu Val Arg Ala Glu Pro Ile Leu Thr Arg

-continued

```
                260                 265                 270
Glu Gln Leu Glu Ala Leu Arg Ala Glu Leu Val Lys Thr Ser Arg Ala
            275                 280                 285

Lys Pro Ala Val Ser Thr Pro Ser Leu Leu Leu Arg Val Leu Phe Cys
        290                 295                 300

Ala Val Cys Gly Glu Pro Ala Tyr Lys Phe Ala Gly Gly Gly Arg Lys
305                 310                 315                 320

His Pro Arg Tyr Arg Cys Arg Ser Met Gly Phe Pro Lys His Cys Gly
                325                 330                 335

Asn Gly Thr Val Ala Met Ala Glu Trp Asp Ala Phe Cys Glu Glu Gln
            340                 345                 350

Val Leu Asp Leu Leu Gly Asp Ala Glu Arg Leu Glu Lys Val Trp Val
        355                 360                 365

Ala Gly Ser Asp Ser Ala Val Glu Leu Ala Glu Val Asn Ala Glu Leu
        370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                405                 410                 415

Gln Glu Glu Leu Glu Gly Leu Glu Ala Arg Pro Ser Gly Trp Glu Trp
            420                 425                 430

Arg Glu Thr Gly Gln Arg Phe Gly Asp Trp Trp Arg Glu Gln Asp Thr
        435                 440                 445

Ala Ala Lys Asn Thr Trp Leu Arg Ser Met Asn Val Arg Leu Thr Phe
        450                 455                 460

Asp Val Arg Gly Gly Leu Thr Arg Thr Ile Asp Phe Gly Asp Leu Gln
465                 470                 475                 480

Glu Tyr Glu Gln His Leu Arg Leu Gly Ser Val Val Glu Arg Leu His
                485                 490                 495

Thr Gly Met Ser
            500
```

RECOMBINATION SYSTEMS FOR HIGH-THROUGHPUT CHROMOSOMAL ENGINEERING OF BACTERIA

RELATED APPLICATIONS

The present invention is a national stage filing under 35 U.S.C. § 371 of international PCT application, PCT/US2019/013381, filed Jan. 11, 2019, which claims priority under 35 U.S.C. § 119(e) to U.S. provisional patent application, U.S. Ser. No. 62/617,165, filed Jan. 12, 2018, the entire contents of each of which are incorporated herein by reference.

BACKGROUND

Current methods for genome engineering in certain types of bacteria (e.g., mycobacteria) rely on relatively inefficient recombination systems that require the laborious construction of a long double-stranded DNA substrate for each desired modification. For example, two different types of recombineering methodologies have been applied to mycobacteria, but neither represents a broadly generalizable approach for genome engineering. Target-specific dsDNA substrates can be used to make diverse and selectable mutations. However, even the smallest useful recombination substrates consist of both a selectable marker and ~500 bp of flanking homology to the chromosome. These dsDNA constructs are cumbersome to generate for each desired mutation, and even these large substrates recombine at relatively low-efficiency. In contrast, single-stranded oligonucleotides are easily synthesized and can be used to alter one or a few bases of the chromosome at high efficiency. However, these mutations are generally not selectable and therefore difficult to isolate.

SUMMARY

In some aspects, the disclosure relates to methods and compositions for genetic engineering of certain types of cells (e.g., bacteria, such as mycobacteria). The disclosure is based, in part, on a combination of genetic recombination systems (e.g., a "targeting oligo" and a "payload plasmid) that enable high-throughput chromosomal engineering and do not involve the preparation of double-stranded DNA (dsDNA) recombination substrates. In some embodiments, a targeting oligo incorporates a Bxb1 phage integrase attP site at a target locus which allows simultaneous integration of a co-transfected payload plasmid comprising a cognate recombination site (e.g., attB site) and a selectable maker into the target locus. The skilled artisan will appreciate, that in some embodiments, methods and compositions described herein are useful for chromosomal engineering of eukaryotic cells, for example mammalian cells (e.g., human cells, rodent cells, etc.), yeast cells, fungal cells, etc.

Accordingly, in some aspects, the disclosure provides a method for genetic modification of a bacterium, the method comprising contacting a bacterium with a single-stranded targeting oligonucleotide comprising an attP attachment site flanked by homology arms that are homologous to a target nucleic acid sequence of the bacterium; and, a non-replicating payload plasmid comprising an attB attachment site and a nucleic acid sequence encoding a selectable marker, wherein a single strand annealing protein (SSAP) and/or an integrase protein is expressed in the bacterium.

In some embodiments, a bacterium is a *Mycobacterium*. In some embodiments, a *Mycobacterium* is *M. tuberculosis* or *M. smegmatis*. In some embodiments, a bacterium is an *E. coli, Pseudomonas* sp., or *Shigella* sp. bacterium. In some embodiments, a population of bacterial cells are contacted with the targeting nucleotide and the non-replicating payload plasmid.

In some embodiments, a homology arm comprises a nucleic acid sequence that is between 25 and 100 bases long. In some embodiments, a homology arm comprises a nucleic acid sequence is between 45 and 75 bases long.

In some embodiments, a single-stranded targeting oligonucleotide comprises a sequence set forth in Table 5.

In some embodiments, an attP attachment site is a Bxb1 attP attachment site. In some embodiments, an attB attachment site is a Bxb1 attB attachment site.

In some embodiments, a selectable marker comprises a nucleic acid sequence encoding a drug resistance gene. In some embodiments, a drug resistance gene is a hyg-resistance gene, a kan-resistance gene, or a zeo-resistance gene.

In some embodiments, a non-replicating payload plasmid comprises a nucleic acid sequence encoding a promoter sequence or a peptide. In some embodiments, a peptide is a C-terminal tag. In some embodiments, a payload plasmid is described in Table 3.

In some embodiments, the integrase protein expressed in a bacterium is Bxb1 phage integrase. In some embodiments, a SSAP expressed in a bacterium is a RecT protein. In some embodiments, RecT protein is a mycobacteriophage RecT protein.

In some embodiments, a bacterium is contacted simultaneously with the single-stranded targeting oligonucleotide and the non-replicating payload plasmid, for example by co-transfection of the targeting oligonucleotide and the payload plasmid into the bacterium.

In some embodiments, a target nucleic acid sequence is located on a bacterial chromosome. In some embodiments, a target nucleotide sequence is located on a bacterial plasmid.

In some embodiments, methods described by the disclosure further comprise the step of culturing bacteria after they have been contacted with a targeting oligonucleotide and a payload plasmid. In some embodiments, methods described by the disclosure further comprise the step of selecting bacteria based upon the presence of a selectable marker.

In some embodiments, contacting a bacterium with a targeting oligonucleotide and a payload plasmid results in a deletion of a target nucleic acid sequence in the bacterium. In some embodiments, contacting a bacterium with a targeting oligonucleotide and a payload plasmid results in insertion of the nucleic acid sequence encoding the promoter sequence or the peptide into the genome of the bacterium.

In some aspects, the disclosure provides an isolated nucleic acid comprising a sequence set forth in Table 5. In some embodiments, the disclosure provides an isolated nucleic acid comprising a sequence encoding a plasmid as described in Table 3 or Table 4.

In some embodiments, the disclosure provides a cell (e.g., a bacterial cell) comprising a single-stranded targeting oligonucleotide and a non-replicating payload plasmid as described herein. In some embodiments, the bacterial cell is a *Mycobacterium* cell. In some embodiments, the cell is an *E. coli, Pseudomonas* sp., or *Shigella* sp. cell.

In some embodiments, a cell further comprises a plasmid encoding a SSAP and/or an integrase protein. In some embodiments, the integrase protein expressed in the cell is Bxb1 phage integrase. In some embodiments, the SSAP expressed in the cell is a RecT protein (e.g., mycobacteriophage RecT protein).

In some aspects, the disclosure provides a population of cells (e.g., bacterial cells), comprising a plurality of cells containing a targeting oligonucleotide and a payload plasmid as described herein.

In some aspects, the disclosure provides a kit comprising: a single-stranded targeting oligonucleotide comprising an attP attachment site flanked by homology arms that are homologous to a target nucleic acid sequence of a bacterium; a non-replicating payload plasmid comprising an attB attachment site and a nucleic acid sequence encoding a selectable marker; and, optionally, a population of bacterial cells.

In some embodiments, the kit further comprises an isolated nucleic acid encoding a single strand annealing protein (SSAP) and/or an integrase protein. In some embodiments, the bacterium expresses a single strand annealing protein (SSAP) and/or an integrase protein.

In some embodiments, the bacterium is a *Mycobacterium*. In some embodiments, the *Mycobacterium* is *M. tuberculosis* or *M. smegmatis*. In some embodiments, the bacterium is an *E. coli, Pseudomonas* sp., or *Shigella* sp. bacterium.

BRIEF DESCRIPTION OF DRAWINGS

FIG. 1A shows a diagram of oligo-mediated recombineering of a chromosomal target in *M. smegmatis*. An integrating plasmid (pKM433) at the L5 phage attachment site contains a hyg-resistance gene with an internal 60 bp deletion (square). Electroporation of an oligo containing the 60 bases missing in the target gene, along with 60 bp of flanking DNA on each side, is electroporated into cells expressing the Che9c RecT function from pKM402. FIG. 1B shows representative data for growth of hyg-resistant bacterial colonies after insertion of a 60 bp loop. The experiment was performed in triplicate; standard errors are shown.

FIGS. 2A-2E show schematic depictions of plasmids constructed for ORBIT. FIG. 2A shows construct pKM444, which expresses the Che9c phage RecT annealase and the Bxb1 phage Integrase, both driven from the Ptet promoter. A similar construct (pKM461) contains (in addition) the sacRB genes for curing the plasmid following gene modification. FIG. 2B shows an ORBIT plasmid (e.g., pKM446) used for integration into the chromosomal attP site created by an oligo. In this case, the plasmid payload contains a Flag-DAS+4 degradation tag that will be fused to the C-terminal end of the target gene. FIG. 2C shows three *M. smegmatis* genes targeted for addition of the Flag-DAS4 peptide to the C-terminal ends. The number of colonies obtained in each transformation ranged from 10-100. Electroporations with payload plasmid only (no targeting oligo) gave, on average, 5-fold fewer total numbers of colonies. On the right, the number of correct recombinants (out of 4 candidates tested) for each target gene is shown. FIG. 2D shows PCR analysis of the 5' junctions of each candidate tested. FIG. 2E shows a schematic depicting the primer positions for verification by PCR of the recombinants are shown; 5' junction and 3' junction are denoted by arrows. In each case where a 5' junction was verified, the 3' junction was also verified. The 5' junctions were confirmed by DNA sequencing.

FIG. 3, top panel, shows the recA-Flag-DAS+4 strain that was transformed with an SspB-producing plasmid pGMCgS-TetON-18 (strep$^R$) under control of the reverse TetR repressor. In this scenario, RecA is proteolyzed in the absence of ATc. Tenfold serial dilutions of the cells were spotted on LB-strep plates and the cells were exposed to 20 J/m2 of UV. In the absence of ATc, increased sensitivity of recA-Flag-DAS+4 strain containing pGMCgSTetON-18 (relative to the tagged strain containing a control plasmid) is observed (top-left). In the presence of ATc, both strains show similar UV sensitivities (top-right). FIG. 3, middle panel, shows the DivIVA-Flag-DAS+4 strain that was transformed with an SspB-producing plasmid pGMCgS-TetOFF-18 (strep$^R$) under control of the wild type TetR repressor. In this case, DivIVA is depleted in the presence of ATc. In the absence of ATc, both cultures grew well on LB-strep plates. In the presence of ATc, growth sensitivity was observed for the DivIVA-Flag-DAS+4 strain containing the SspB-producer. FIG. 3, bottom panel, shows the same conditions as the middle panel, except that leuB is the target and the cells are plated on 7H9 plates.

FIG. 5A shows the amount of target homology flanking the attP site in an oligo designed to create a polA-Flag-DAS fusion in *M. smegmatis*. Fusion of the target gene to polA was examined as a function of recombinant formation (as measured by Hyg$^R$). The frequency of targeting is expressed as the percentage of Hyg$^R$ transformants following integration of pKM446 relative to a transformation control (0.1 µg of Gen$^R$ plasmid pKM390). PCR analysis revealed that 39/40 Hyg$^R$ transformants (8 from each oligo) contained the Fag-DAS+4 fusion. Experiments were performed in triplicate; standard errors are shown. FIG. 5B shows colony counts measured after electroporation of 1 µg of an oligo with 70 base flanks (designed to create a polA-Flag-DAS+4 fusion) with various amounts of pKM446. CFU/ml was measured following overnight growth of the electroporation mixtures in 2 ml LB.

FIG. 8A shows a diagram of ORBIT-generated promoter replacement. In the non-replicating plasmid, the promoter to be inserted into the chromosome is placed to the left of the attB site. A TrrnB terminator is placed upstream of this promoter to prevent read-through from the plasmid backbone. The oligo is designed to place attP just upstream of the target gene in place of the endogenous promoter. Following integration, the promoter and inserted ribosome binding site drive expression of the chromosomal target gene (lacZ). FIG. 8B shows ORBIT was carried out with plasmids pKM496 ($P_{GroEL}$), pKM508 ($P_{imyc}$) and pKM509 (P38) with an oligo that deletes the endogenous promoter. Extracts of the cells were made and beta-galactosidase assays were performed in triplicate (standard error bars shown). The higher amounts of beta-galactosidase present in the engineered strains, relative to the starting strain, is due, in some embodiments, to the presence of the optimized ribosome binding site following each promoter.

DETAILED DESCRIPTION

Figure 1A:
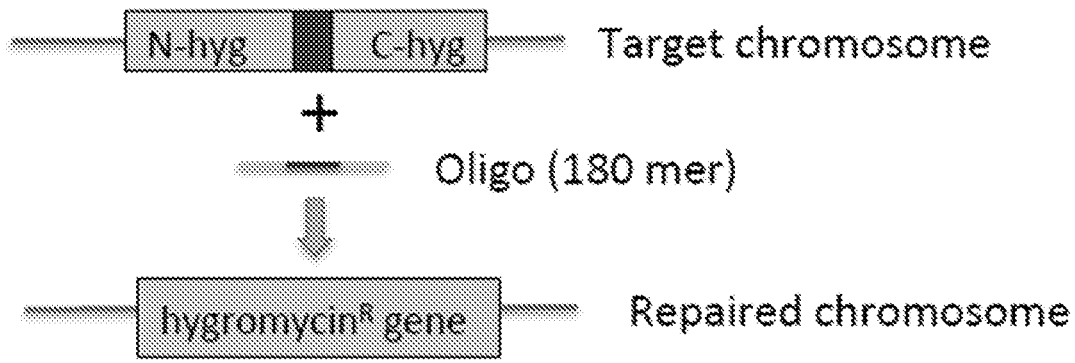
FIGS. 1A-1B show RecT-promoted oligo-mediated 60 base insertion.

Aspects of the disclosure relate to a method for bacterial genetic modification known as Oligo Recombineering followed by Bxb1 Integrase Targeting (ORBIT). In some embodiments, ORBIT methods comprise contacting a bacterium (e.g., a *Mycobacterium* cell or cells) with a single-stranded targeting oligonucleotide comprising a Bxb1 bacteriophage attachment site flanked by homology arms and a payload plasmid comprising a bacterial attachment site. The bacteriophage genome is inserted into the bacterial genome at the target nucleic acid sequence through the action of a single strand annealing portion and/or an integrase protein expressed in the bacterium. In some embodiments, the payload plasmid comprises a nucleic acid sequence encoding a selectable marker and/or a gene product (e.g., protein inhibitory nucleic acid, etc.), allowing the genetic modification and selection of modified bacteria in a single step.

Isolated Oligonucleotides and Nucleic Acids

A "nucleic acid" sequence refers to a DNA or RNA sequence. In some embodiments, nucleic acids of the disclosure are isolated. As used herein, the term "isolated" means artificially produced or purified. As used herein with respect to nucleic acids, the term "isolated" generally means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable manipulated by using recombinant DNA techniques that are well known in the art. A nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulated by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.). In some embodiments, an isolated nucleic acid comprises a sequence set forth in Table 5 or SEQ ID NO: 12-78.

In some aspects, the disclosure provides single-stranded targeting oligonucleotides that are used to genetically modify a bacterium. An "oligonucleotide" refers to a short DNA or RNA sequence that may be synthesized. "Targeting" refers to directing an oligonucleotide to a target nucleic acid sequence of interest. In some embodiments, the single-stranded targeting oligonucleotide sequence comprises or consists of a sequence selected from Table 5 or SEQ ID NO: 12-78. In some aspects, the disclosure provides homology arms flanking the single-stranded oligonucleotide. In some embodiments, the homologous arms are between 25 and 100 bases long. In some embodiments, the homologous arms are optionally between 45 and 75 base pairs long.

Genetic Engineering in Bacterial Cells

Bacterial recombineering (recombination-based genetic engineering) is in vivo genetic engineering of bacterial cells. Modifications to the bacterial genome in recombineering are typically catalyzed by phage recombination proteins produced within the bacterial cells. "Bacteriophage" or "phage" is a virus that infects and replicates within bacteria after inserting its genome. Examples of bacteriophages include, but are not limited to: phage lambda, which infects *E. coli*, and Bxb1, which infects *Mycobacterium* species.

"Recombination" refers to the highly accurate artificial joining of complementary nucleotide sequences of DNA from different organisms. Recombination proteins, such as single strand annealing proteins or integrases, allow for the efficient introduction of sequences to or deletion of sequences from the bacterial genome. In some embodiments, recombination can be efficiently performed between pairs of oligonucleotides or nucleic acids comprising as few as 30 contiguous homologous base pairs or nucleotides. In some embodiments, recombination occurs between a target nucleic acid sequence and an exogenous oligonucleotide. As used herein, "homologies" and "homology" refer to regions of complementarity between two or more nucleic acids. In some embodiments, complementarity refers to nucleobase pairings between, for example, purine and pyrimidine bases. In some embodiments, homologous regions of a pair of oligonucleotides or nucleic acids may be at least 75%, at least 80%, at least 85%, at least 90%, at least 95%, or 100% complimentary. In some embodiments, homologous regions of a pair of oligonucleotides or nucleic acids may be at least 10, at least 20, at least 30, at least 40, at least 50, at least 60, at least 70, at least 80, at least 90, or at least 100 nucleotides in length. In some embodiments, homologous regions of a pair of oligonucleotides or nucleic acids are 25-100, 25-50, 50-100, 45-75, 45-60, or 60-70 nucleotides in length. In some embodiments, homologous regions of a pair of oligonucleotides or nucleic acids are 45, 60, or 70 nucleotides in length. In some embodiments, a pair of oligonucleotides or nucleic acids comprise a homology arm, e.g., a homology arm that flanks, or is adjacent to, an attP attachment site, and a target nucleic acid sequence, e.g., an endogenous bacterial gene to be modified.

An "exogenous" biological agent, e.g., protein or nucleic acid, is a biological agent that originates from outside an organism, for example a heterologous nucleic acid or protein. An "endogenous" biological agent, e.g., protein or nucleic acid, is a biological agent that originates from within an organism, for example is encoded by a nucleic acid in the genome of an organism and/or is naturally expressed by an organism.

A method for bacterial genetic modification by phage is provided by the disclosure. The nucleic acid sequence to be modified is encoded in a single-stranded oligonucleotide and is flanked by lambda phage attachment attP sites. The attP sites are flanked by targeting sequences which are complementary to the regions on the bacterial genome to be modified. The payload plasmid in the instant disclosure comprises an attB bacterial attachment site. Site-specific recombination occurs when a phage integrase protein or an annealase proteins such as RecT or single strand annealing protein bind to the attP and attB attachment sites and catalyze modification of the bacterial genome.

In some aspects, methods described by the disclosure comprise contacting a bacterium (or a population of bacteria) with a single stranded oligonucleotide comprising a phage attachment site, for example an attP attachment site. An attP attachment site is a nucleic acid sequence that may undergo recombination with another phage attachment site, for example an attB attachment site. An attP attachment site is capable of interacting, associating or binding to a recombinase protein, such as an integrase, e.g., a Bxb1 integrase. Phage attachment sites, such as attP attachment sites, attB attachment sites, and recombinase proteins that bind to them are described, for example by Amy C. Groth and Michele P. Calos, "Phage Integrases: Biology and Applications" *Journal of Molecular Biology*, Volume 335, Issue 3, 16 Jan. 2004, Pages 667-678; VIRGINIA BARREIRO AND ELISABETH HAGGARD-LJUNGQUIST and, "Attachment Sites for Bacteriophage P2 on the *Escherichia coli* Chromosome: DNA Sequences, Localization on the Physical Map, and Detection of a P2-Like Remnant in *E. coli* K-12 Derivatives" JOURNAL OF BACTERIOLOGY, Vol. 174, No. 12, p. 4086-4093, June 1992.). Phage attachment sites generally are complementary to a cognate phage attachment site. For example, in some embodiments, an attP attachment site is complimentary or otherwise homologous to its cognate attB attachment site. In some embodiments, an attP attachment site is 15-75, 15-50, 15-30, 30-50, 40-50, or 48 nucleotides in length. In some embodiments, an attP attachment site associates with Bxb1 integrase. In some embodiments, an attP attachment site comprises SEQ ID NO: 79 (GGTTTGTACCGTACACCACTGA-GACCGCGGTGGTTGACCAGACAAACC). In some embodiments, an attP attachment site comprises a core sequence that is complimentary or otherwise homologous to an attB attachment site. In some embodiments, the core sequence of an attP attachment site is 6, 7, 8, 9, 10, 11, or 12 nucleotides in length. In some embodiments, the core sequence of an attP attachment site is "-GCGGTCTC-". In some embodiments, a phage attachment site (e.g., a first phage attachment site or a second phage attachment site) comprises the sequence "-GCGGTCTC-".

In some embodiments, an attP attachment site is flanked by homology arms. As used herein, "homology arms" refer to a pair of single-stranded nucleic acids that flank (e.g., are located on either side of) a phage attachment site, for example an attP attachment site. In some embodiments, homology arms are homologous to two neighboring regions of a target nucleic acid sequence, i.e., one homology arm is homologous is complimentary to a first region of a target gene; the second homology arm is homologous to a second region of the same target gene. In some embodiments, each homology arm binds to a target nucleic acid that is to be modified. In some embodiments, binding of a pair of homology arms to a complimentary pair of regions of a target nucleic acid enables subsequent recombination, e.g., leading to a genetic deletion, at said target nucleic acid. In some embodiments, a homology arm is be at least 75%, at least 80%, at least 85%, at least 90%, at least 95%, or 100% complimentary to a region of a target nucleic acid. In some embodiments, a homology arm is 25-100, 25-50, 50-100, 45-75, 45-60, or 60-70 nucleotides in length. In some embodiments, a homology arm is 100-250, 200-500, 500-1,000, or more nucleotides in length. In some embodiments, a homology arm is 45, 60, or 70 nucleotides in length.

Homology arms may share identity (e.g., homology or complementarity) with regions of a target nucleic acid sequence. As described herein, a target nucleic sequence is a nucleic acid sequence, e.g., an endogenous nucleic acid sequence or genetic locus, such as a gene, present in the genome of a bacteria. Non-limiting examples of target nucleic acid sequences include genes encoding recD, recF, recG, recO, ruvC, recR, nusS, rhlE, and deadD genes in *M. smegmatis*, and genes encoding cmaA2, mmaA1, TB8.4, Rv1184c, Rv1273c, cinA, PPE51, Rv3822, Rv1747, Rv0248c, Rv0249c, glpK, Rv1543, CydD, CydA, Pks12, arsA, Rv3680, Rv2047, FadE5, Rv1488, NarG-NarI, Rv0465c, cyd operon, mbtA, mbtB, sseA, ctpC, pstS3, pstC2, EccB1, Rv2563, Rv2564, fadE28, kstR, nucS, rhiE, lhr, deaD, grcC2, Rv1592 in *M. tuberculosis*. In some embodiments, a target nucleic acid sequence is located within the genome of a bacterium, e.g., on a bacterial chromosome.

In some aspects, methods described by the disclosure comprise contacting a bacterium (or a population of bacteria) with a payload comprising a nucleic acid encoding an attB attachment site and a selectable marker. In some embodiments, a payload is situated on a plasmid (e.g., a bacterial plasmid), and may be referred to as a plasmid payload. As used herein the term "plasmid" is a genetic element capable being transferred between cells, e.g., using electroporation or heat shock. In some embodiments, a plasmid payload is located on a non-replicating plasmid, such as a plasmid as that lacks (i.e., does not possess) an origin of replication. In some embodiments, a non-replicating plasmid is a circular DNA plasmid that it is incapable of being replicated by its host bacterium. In some embodiments, the attB attachment site is located at or downstream of the 3' end of the selectable marker. In some embodiments, the attB attachment site is located at or upstream of the 5' end of the selectable marker.

An attB attachment site is a nucleic acid sequence that may undergo recombination with an attP attachment site. Typically, an attB attachment site is capable of interacting, associating or binding to a recombinase protein, such as an integrase, e.g., a Bxb1 integrase. In some embodiments, an attB attachment site is complimentary or otherwise homologous to its cognate attP attachment site. In some embodiments, an attB attachment site associates with Bxb1 integrase. In some embodiments, an attB attachment site comprises a core sequence that is complimentary or otherwise homologous to an attP attachment site. In some embodiments, the core sequence of an attB attachment site is 6, 7, 8, 9, 10, 11, or 12 nucleotides in length. In some embodiments, the core sequence of an attB attachment site identical, homologous, or complimentary to "-GCGGTCTC-".

A "selectable marker" generally refers to a nucleic acid encoding a protein or gene that, when introduced into a bacterium, provides the bacterium with a trait that allows for artificial selection. In some embodiments, a selectable marker is a positive selectable marker, e.g., a protein or gene that confers a competitive advantage to a bacterium that contains the marker, a negative selectable marker, e.g., a protein or gene that the growth and/or division of a bacterium that contains the marker, or a mixed positive/negative selectable marker, e.g., a protein or gene that can provide a competitive advantage under certain circumstances and deleritious fitness effects under other circumstances. In some embodiments, a selectable marker can be used to isolate a particular bacterium which has been genetically modified from those which have not been genetically modified. In some embodiments, the selectable marker sequence encodes a drug or antibiotic resistance gene. In some embodiments, a drug resistance gene comprises a hygromycin-resistance gene, a kanamycin-resistance gene, ampicillin-resistant gene, streptomycin-resistant gene, or a zeocin-resistance gene. In some embodiments, the selectable marker encodes thymidine kinase. The methods described herein may be utilized with any suitable selectable marker.

In some embodiments, a payload further comprises a nucleic acid encoding a gene product. A gene product may be a peptide, protein, polypeptide, or inhibitory nucleic acid (e.g., dsRNA, siRNA, shRNA, miRNA, etc.). Non-limiting examples of peptide, protein, or polypeptides for use in the methods described include aceE, Rv0218, dnaE2, acn, dppD, pknE, Rv0228, pabB, Rv0556, galU, rmlC, Rv3034c, glyA1, cysW, ssb, moeB1, thiL, Rv3910, mrsA, gcpE, guaB3, pgsA3, metK, Rv3034c, cpsA, gltA2, hupB, and ispF. In some embodiments, a nucleic acid sequence encoding a gene product is operably linked to a promoter sequence and/or operably linked to a nucleic acid sequence encoding the selectable marker.

In some embodiments, a peptide or polypeptide encoded by the payload (e.g., a payload plasmid) further comprises a N-terminal or C-terminal tag, e.g., solubility tag, reporter tag, or purification tag. Non-limiting examples of N-terminal or C-terminal tags include FLAG, eGFP, mVenus, SNAP, CLIP, Myc epitopes, His epitopes, TEV cleavage sites, etc. In some aspects, the payload plasmid that comprises a C-terminal peptide tag is listed in Table 3.

A "promoter" is a DNA sequence recognized by the synthetic machinery of the cell, or introduced synthetic machinery, required to initiate the specific transcription of a gene. In some embodiments, the payload (e.g., payload plasmid) further comprises a nucleic acid sequence encoding a promoter, e.g., a constitutive promoter or an inducible promoter. Non-limiting examples of promoters for use in the methods described include $P_{imyc}$ promoter, $P_{GroEL}$ promoter, P38 promoter, anhydrotetracycline (ATc)-inducible $P_{tet}$, hyg promoter, etc.

Aspects of the disclosure relate to methods of contacting a bacterium with a single-stranded targeting oligonucleotide and a payload (e.g., a non-replicating payload plasmid) in the presence of a single strand annealing protein (SSAP) and/or an integrase protein. An SSAP and/or an integrase may be expressed naturally by a bacterium, for example by being encoded by the genome of the bacterium (i.e., endogenously) or expressed by a bacteriophage present in the bacterium, or introduced into the bacterium in the form of an expression vector (e.g., heterologously-expressed in the bacterium).

As used herein, a "single strand annealing protein" or "SSAP" refers to recombinase protein that is capable of binding to terminal ends of single-stranded nucleic acids such as DNA and mediating nucleic acid interactions necessary for the annealing of complementary nucleic acid strands. Examples of SSAPs include but are not limited to RecT (e.g., a RecT from *Mycobacterium* phage, e.g., NCBI Accession Number: YP_009198391), RAD52 (e.g., a RAD52 from *Saccharomyces cerevisiae*, e.g., NCBI Accession Number: CAA86623) and Redo from X phage. In some embodiments, an SSAP interacts with an attP and/or attB attachment site. In some embodiments, RecT is represented by the amino acid sequence set forth below:

```
RecT (Mycobacterium phage; NCBI Accession
Number: YP_009198391)
                                    (SEQ ID NO: 80)
MTSTEVAKNTDAEPTLPQLIQQMKPEIAKALPAQMNPERMARIATTVLKQ

TPALARCTPASFLGALMTASQLGLEPGPLGESYFVPYGKDVTFIPGYRGL

IKLARNSGLLVDIWAEIVYANDEFKYTLGLHRDLQHVPATGDRGKPIYVY

AAAKLKDGGTPFVVMTHAEVEAIRARSRAGKNGPWVTDWNAMAKKTAVKQ

LAKWLPLSAEFNTATVMDGTVRSDYTSNLIDVKPEYIDGEVDDNATDPEP

AEMVPDTDPNVIDGEATEIRMASKDQLKRLSEIQRAEKYTDEDWFTFLAE

AAGVQATRAGELTFEEATRAIAVFDGPDL
```

In some embodiments, a bacterium is contacted with an integrase protein. Generally, integrase proteins are enzymes that mediate site-specific recombination between two nucleic acid recognition sequences, for example attP and its cognate attB. Integrases may be tyrosine recombinases or the serine recombinases. Examples of integrase proteins include but are not limited to Bxb1 integrase (e.g., NCBI Accession Number: AAG59740), λ integrase, TP 901-1 integrase, φBT1 integrase, R4 integrase, MR11 integrase, A118 integrase, φK38 integrase, φC31 integrase, Wβ integrase and SPBC integrase. In some embodiments, the integrase protein is a Bxb1 integrase, for example as set forth below:

```
Bxb1 integrase (e.g., NCBI Accession Number:
AAG59740),
                                    (SEQ ID NO: 81)
MRALVVIRLSRVTDATTSPERQLESCQQLCAQRGWDVVGVAEDLDVSGAV

DPFDRKRRPNLARWLAFEEQPFDVIVAYRVDRLTRSIRHLQQLVHWAEDH

KKLVVSATEAHFDTTTPFAAVVIALMGTVAQMELEAIKERNRSAAHFNIR

AGKYRGSLPPWGYLPTRVDGEWRLVPDPVQRERILEVYHRVVDNHEPLHL

VAHDLNRRGVLSPKDYFAQLQGREPQGREWSATALKRSMISEAMLGYATL

NGKTVRDDDGAPLVRAEPILTREQLEALRAELVKTSRAKPAVSTPSLLLR

VLFCAVCGEPAYKFAGGGRKHPRYRCRSMGFPKHCGNGTVAMAEWDAFCE

EQVLDLLGDAERLEKVWVAGSDSAVELAEVNAELVDLTSLIGSPAYRAGS

PQREALDARIAALAARQEELEGLEARPSGWEWRETGQRFGDWWREQDTAA

KNTWLRSMNVRLTFDVRGGLTRTIDFGDLQEYEQHLRLGSVVERLHTGMS
```

In some embodiments, methods described by the disclosure allow for genetic modification, e.g., insertions and/or deletions of nucleic acid sequence or genes, at a target nucleic acid sequence or locus. In some embodiments, the methods described herein involve the deletion of target gene, a target gene promoter, the knockdown of a target gene, or the knockout of a target gene. In some embodiments, the methods described herein involve the insertion of an exogenous nucleic acid, e.g., a nucleic acid encoding a gene product as described, into a target nucleic acid sequence of a bacterium.

Bacterial Cells

In some aspects, the disclosure relates to methods for genetic modification of a bacterium. In some embodiments, methods described by the disclosure relate to genetic modification of a plurality (e.g., a population) of bacterial cells. Examples of bacterial cells include but are not limited to Escherichia coli (E. coli), Pseudomonas aeruginosa (P. aeruginosa), Staphylococcus aureus (S. aureus), Streptococcus pneumoniae (S. pneumoniae), Mycobacterium tuberculosis (M. tuberculosis), Mycobacterium leprae (M. leprae), Mycobacterium smegmatis (M. smegmatis), etc. Generally, a population of bacterial cells may comprise between 2 and $10^{10}$ bacterial cells, for example 2-10, 10-100, 10-$10^3$, 100-$10^3$, $10^2$-$10^3$, $10^3$-$10^4$, $10^3$-$10^5$, $10^4$-$10^5$, $10^4$-$10^6$, $10^5$-$10^7$, $10^5$-$10^6$, $10^6$-$10^8$, $10^6$-$10^7$, $10^7$-$10^9$, $10^7$-$10^8$, $10^8$-$10^{10}$, $10^8$-$10^9$, or $10^9$-$10^{10}$ bacterial cells. In some embodiments, a population of bacterial cells is a homogenous population, i.e., all bacterial cell belong to the same species. In some embodiments, a population of bacterial cells is a heterogeneous population, i.e., bacterial cells belong to at least two different species. In some embodiments, a heterogeneous population may comprise 2, 3, 4, 5, 6, 7, 8, 9, 10, or more different bacterial species.

In some aspects, the disclosure provides a bacterial cell (e.g., a bacterial cell that has been modified by methods described by the disclosure, such as a genetically-modified bacterial cell). A bacterial cell is a single prokaryotic cell. Examples of prokaryotic species include (but are not limited to): Escherichia coli (E. coli), Pseudomonas aeruginosa (P. aeruginosa), Staphylococcus aureus (S. aureus), Streptococcus pneumoniae (S. pneumoniae), Mycobacterium tuberculosis (M. tuberculosis), Mycobacterium leprae (M. leprae), Mycobacterium smegmatis (M. smegmatis), etc. In some embodiments, the bacterium is a Mycobacterium. In some embodiments, the Mycobacterium is M. tuberculosis. In some embodiments, the Mycobacterium is M. smegmatis.

In some aspects, the disclosure provides a population of bacterial cells, comprising a plurality of bacterial cells. Examples of bacterial species include (but are not limited to): Escherichia coli (E. coli), Pseudomonas aeruginosa (P. aeruginosa), Staphylococcus aureus (S. aureus), Streptococcus pneumoniae (S. pneumoniae), Mycobacterium tuberculosis (M. tuberculosis), Mycobacterium leprae (M. leprae), Mycobacterium smegmatis (M. smegmatis), etc. In some embodiments, the population of bacterial cells comprise mycobacteria. In some embodiments, the mycobacteria are M. tuberculosis. In some embodiments, the mycobacteria are M. smegmatis.

In some embodiments, a bacterial cell is a Mycobacteria cell. Mycobacteria belong to a genus of Actinobacteria known as Mycobacteriaceae. Mycobacterial species are human pathogens that cause serious disease including tuberculosis (Mycobacterium tuberculosis), as well as non-pathogenic species such as Mycobacterium smegmatis. The cell wall surrounding mycobacteria is hydrophobic, waxy, and thicker than in many other bacteria. The difficulty in penetrating this thick cell wall likely contributes to the hardiness of mycobacterial infections. Some aspects of the instant disclosure provide methods for genomic modification of mycobacterial species utilizing Bxb1 mycobacteriophage, which penetrates the thick cell wall of Mycobacterium.

In some aspects, the disclosure provides culturing bacteria. The term "culturing" is used to describe the maintenance of bacteria in growth media to promote bacterial cell survival and proliferation. In some embodiments, bacterial cells may be cultured prior to being contacted nucleic acids as described by the disclosure. In some embodiments, bacterial cells may be cultured following contact with the nucleic acids as described herein.

In some embodiments, cultured bacterial cells are selected based upon the presence of the selectable marker introduced by the payload (e.g., payload plasmid). Cells may be cultured in a monolayer or in a suspension. Cells may be cultured at any temperature at which the cells are capable of survival. In some embodiments, cells may be cultured at 37° C. As outlined above, selectable markers are nucleic acid sequence which encode genes that can be used to isolate bacteria which have been genetically modified from those which have not been genetically modified. In some embodiments, the selectable marker sequence encodes a drug resistance gene.

In some aspects, the drug resistance gene comprises a hyg-resistance gene (e.g., Hygromycin B phosphotransferase (Hph), NCBI Gene ID: 20473139), a kan-resistance gene (e.g., aphA1, NCBI Gene ID: 6384255) or a zeo-resistance gene (e.g., a nucleic acid encoding Bleomycin resistance protein from Streptoalloteichus hindustanus, NCBI Accession Number: P17493). A "hyg-resistance gene" encodes for a protein that would render a bacterium that expresses it resistant to the antibiotic hygromycin. In some embodiments, selecting for bacterial cells that have integrated the hyg-resistance gene is culturing bacterial cells in the presence of hygromycin. A "kan-resistance gene" encodes for a protein that would render a bacterium that expresses it resistant to the antibiotic kanamycin. In some embodiments, selecting for bacterial cells that have integrated the kan-resistance gene is culturing bacterial cells in the presence of kanamycin. A "zeo-resistance gene" encodes for a protein that would a bacterium that expresses it resistant to the antibiotic zeocin. In some embodiments, selecting for bacterial cells that have integrated the zeo-resistance gene is culturing bacterial cells in the presence of zeocin. In some aspects, methods described herein are useful for the selection of cultured bacterial cells devoid of any antibiotic resistance markers.

Modes of Delivery

In some aspects of the disclosure, a bacterium is contacted with a single-stranded oligonucleotide targeting molecule and a payload plasmid. In some embodiments, the term "contacted" and the variation "contact" are used herein to refer to a bacterium being directly associated with (i) a single-stranded targeting oligonucleotide comprising an attP attachment site flanked by homology arms that are homologous to a target nucleic acid sequence of the bacterium; and (ii) a non-replicating payload plasmid comprising an attB attachment site and a nucleic acid sequence encoding a selectable marker. In some embodiments, a bacterium is contacted simultaneously with a single-stranded targeting oligonucleotide and a non-replicating payload plasmid. In some embodiments, a bacterium is contacted sequentially with a single-stranded targeting oligonucleotide and a non-replicating payload plasmid, in any order of operation.

In some embodiments, contacting comprises co-transfection of the targeting oligonucleotide and the payload plasmid. The term "transfection" is used to describe the uptake of foreign DNA by a cell and a cell has been "transfected" when exogenous DNA has been introduced inside the cell membrane. The term "co-transfected" is used to describe the simultaneous uptake of more than one molecule of foreign DNA by a cell. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. In some embodiments, the disclosure provides for the simultaneous transfection of a single-stranded targeting oligonucleotide and a payload plasmid into a bacterial cell.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

EXAMPLES

Example 1: Materials and Methods

Bacterial Strains

*M. smegmatis* strain used in this example were derived from mc2-155; the *M. tuberculosis* strains were all derived from H37Rv.

Media

*M. smegmatis* was grown in Middlebrook 7H9 broth with 0.05% Tween 80, 0.2% glycerol, 0.5% BSA, 0.2% dextrose, and 0.085% NaCl; transformants were selected on LB plates (DIFCO) with appropriate drugs. *M. tuberculosis* was grown in 7H9 broth with 0.05% Tween 80, 0.2% glycerol and OADC; transformants were selected on 7H10 plates with 0.5% glycerol and OADC. When needed, antibiotics were added at the following concentrations: kanamycin (20 µg/ml), streptomycin (20 µg/ml), hygromycin (50 µg/ml), zeocin (25 µg/ml).

Plasmids Plasmids containing the $P_{imyc}$ promoter, the $P_{GroEL}$ promoter and P38 promoter were obtained, as were plasmids pGMCgS-TetOFF-18 and pGMCgS-TetON-18, where the *E. coli* sspB adapter protein is under control of the wild type and reverse TetR repressors, respectively. Plasmids constructed for this study are described in Tables 3 & 4.

Oligos

Oligos used for ORBIT were obtained from IDT as Ultramers at a concentration of 100 M and delivered in 96-well plates; they were supplied desalted with no further purification. Oligos were diluted ten-fold in 10 mM Tris-HCl, pH 8.0, and final concentrations (250-350 ng/ml) were determined by Abs260 using a conversion factor of O.D. of 1=20 µg/ml oligo. ORBIT plasmids (200 ng) were mixed with 1 µg of oligo prior to electroporation.

Design of the ORBIT Oligo

Figure 9:
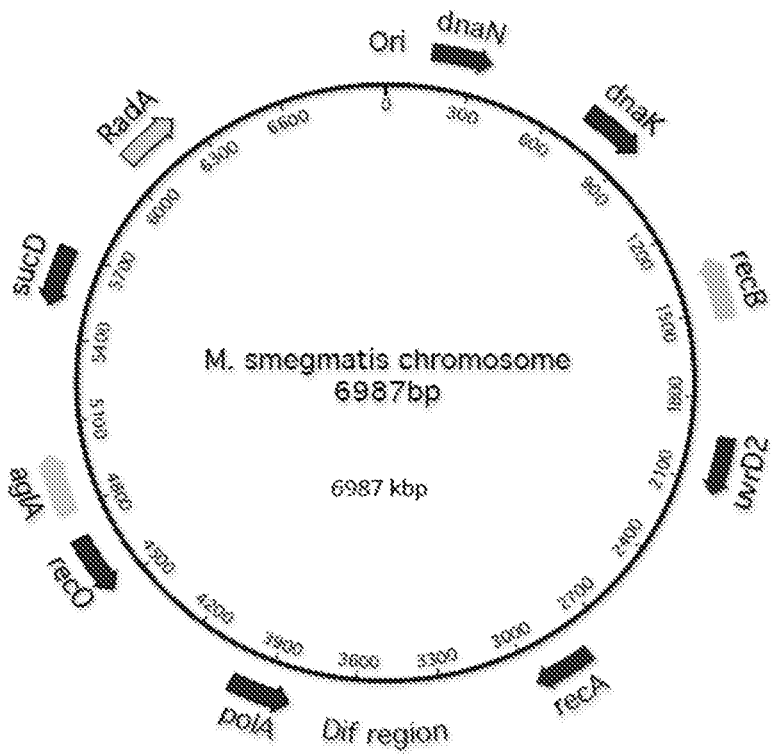
FIG. 9 shows a schematic depicting design of the ORBIT oligo. To identify the lagging strand from a sequence file of a target gene (reading from the start codon 5' to 3'), an attP site is first inserted into the desired position. Then, if the target gene is transcribed toward the Ori sequence, the top strand is used. If the target gene is transcribed toward the Dif region, the bottom strand is used. Bxb1 attP sequence (SEQ ID NO: 79) is also depicted.

The sequence of oligos flanking the attP site used for ORBIT was derived from the lagging strand of the replication fork. For design of an ORBIT oligo, prepare a dsDNA sequence file of a target gene, starting 200 bp upstream of the initiation codon and ending 200 bp downstream of the stop codon. Insert the Bxb1 attP site shown in FIG. 9 into the target sequence file for the type of modification required (i.e., knockout, C-terminal tag, or promoter replacement) as described herein. If the chromosomal position of the gene target is pointing toward the chromosomal origin in either replicore, then select the top strand (5' to 3') of the "target sequence+attP" file as the lagging strand DNA in the oligo. If the chromosomal position of the target gene is pointing away from the chromosomal origin in either replicore, then select the bottom strand (5' to 3') of the "target sequence+attP" file as the lagging strand in the oligo. Example shown in FIG. 9 is for *M. smegmatis*. Apply the same rules of Mtb, but assume the Dif region occurs at 2.2 Mb.

ORBIT Electroporations

A culture of *M. smegmatis* containing plasmid pKM444 (or pKM461) was started overnight by adding 100-150 µl of a fresh saturated stock culture to 20 ml of 7H9 media containing 20 µg/ml kanamycin in a 125 ml flask. Cells were grown on a swirling platform at 37° C. The next day, at an O.D. (600 nm) of 0.5, anhydrotetracycline (ATc) was added to a final concentration of 500 ng/ml. The culture was placed back on the swirling platform at 37° C. for 2.75-3 hours until the culture O.D. was ~1.0. The culture was placed on ice (with swirling) for 10 min and then centrifuged at 4000 rpms for 10 min in a chilled centrifuge. The supernatant was removed, the cells were gently resuspended in 1 ml of 10% cold glycerol and brought up to 20 ml with 10% cold glycerol. The centrifugation and washing steps were repeated. After the second wash, the cells were collected by centrifugation and resuspended in 2 ml of 10% cold glycerol. Aliquots of electrocompetent cells (380 µl) were added to sterile Eppendorf tubes containing 1 µg of an attP-containing oligo and 200 ng of an attB-containing plasmid (except where noted otherwise in figure legends). The cells and DNA were mixed by pipetting and transferred to ice-cooled electroporation cuvettes (0.2 cm). The cells were shocked with an electroporator at settings of 2.5 kV, 1000 OHMs and 25 µF. Following electroporation, the cells were resuspended in 2 ml 7H9 media and rolled at 37° C. overnight. The following day, two 0.5 ml portions of the culture were spread on LB plates containing 50 µg/ml hygromycin or 25 µg/ml zeocin. Recombinant colonies were picked into 2 ml 7H9 media containing 50 µg/ml hygromycin or 25 µg/ml zeocin and grown overnight at 37° C.

Electroporations with *M. tuberculosis* (MTb) was done in a similar manner, with the following modifications. Cells containing pKM444 (or pKM461) were grown in 30 ml 7H9 media containing OADC, 0.2% glycerol, 0.05% tween, and 20 µg/ml kanamycin. At an O.D. of ~0.8, ATc was added to the culture to a final concentration of 500 ng/ml. After ~8 h of swirling at 37° C., 3 ml of 2 M glycine was added to the culture. The cells were shaken at 37° C. overnight (16-20 total hours following induction), collected by centrifugation and processed as described above, except that washes consisted of 30 ml 10% glycerol and all steps were performed at room temperature. Recombinant colonies were picked into 5 ml 7H9-OADC-tween containing 50 µg/ml hygromycin and grown with shaking for 4-5 days at 37° C.

PCR Analysis for Verification of Recombinants

Figure 2A:
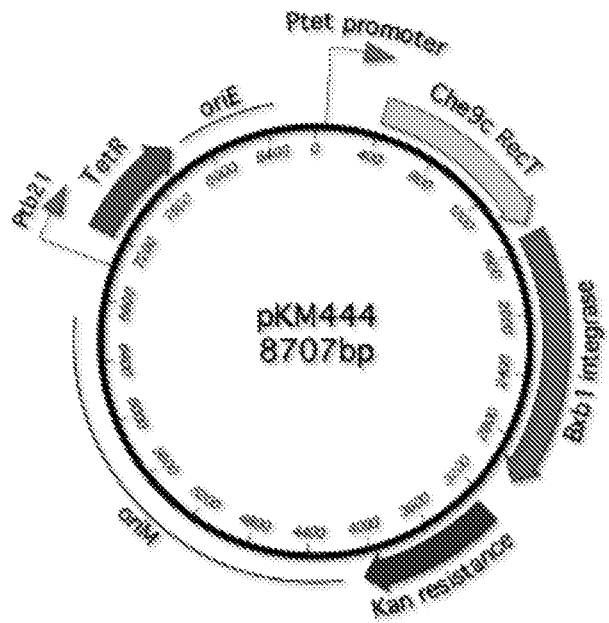

Recombinants were verified by PCR analysis; Taq polymerase was obtained from Denville Scientific, Inc. PCR reactions were performed in 30 µl volume and contained 125 µM dNTPs, 5% DSMO, 1 µM primers, 2 µl of *M. smegmatis* overnight culture (or heat-inactivated Mtb culture) and 0.2 µl of Taq polymerase. Mtb cells (O.D. around 1.5) were heat inactivated at 85° C. for 50 minutes prior to removal form the BSL3 lab. The PCR program consisted of an initial step of 95° C. for 5 minutes (to lyse the cells), thirty cycles of 30 sec at 95° C., 30 sec at 58° C., and 1 minute at 72° C., and a final polymerization step for 5 min at 72° C. Correct sized PCR fragments were generated from both junctions of the plasmid insertion into the chromosome (see FIG. 2E). In each case, the 5' junction was verified by a target specific primer and an "oriE" primer (CCTGGTATCTT-TATAGTCCTGTCG) (SEQ ID NO: 1); the 3' junction was verified by a target specific primer and a "HygC-out" primer (TGCACGGGACCAACACCTTCGTGG (SEQ ID NO: 2) or GAGGAACTGGCGCAGTTCCTCTGG (SEQ ID NO: 3)). In some cases, the 5' junction PCR was verified by sequencing. Target specific primers contained sequences at least 100 bp upstream (5') and downstream (3') of the chromosomal sequences flanking the attP site in the ORBIT oligo. For knockouts, an additional PCR was performed to verify the absence of the target gene in the recombinant.

Fluorescence Microscopy

Bacterial cells were mounted on 1% agar pads and imaged with a DeltaVision Personal DV microscope followed by deconvolution using SoftwoRx software (Applied Precision). Further processing was performed using FIJI software. Image brightness and contrast were adjusted for visibility and the files were converted to 600 dpi. Representative cells are shown from multiple images of each strain.

Beta-Galactosidase Activity Assay

A 5 mL of culture at 0.8-1.0 OD was pelleted and resuspended in 1 mL of freshly prepared Z buffer (50 mM $Na_2HPO_4$, pH 7.0, 10 mM KCl, 1 mM $MgSO_4$, 50 mM β-mercaptoethanol). Cells were lysed by bead beating 4 times at 6.5 M/s for 30 seconds followed by centrifugation for 10 minutes to harvest the supernatant. Protein concentrations were measured with a Nanodrop. For the activity assay, 10 µg of protein and Z buffer (total volume of 100 µL) was added in triplicate to a 96 well microplate. The reaction was started with 20 µL of 4 mg/mL ONPG in 0.1 M, pH 7.0 sodium phosphate buffer. Once sufficient yellow color had developed, the reaction was terminated with 50 µL of 1 M sodium carbonate. Final absorbance of the sample was measured at 420 nm in a plate reader.

Example 2: RecT-Promoted Oligo-Mediated Recombineering—60 bp Insertion

This example describes methods that leverage easily synthesized and highly efficient oligonucleotide substrates to make selectable mutations in bacteria by encoding a phage attachment site (attP) in the oligo that could be used to integrate a selectable marker at a specific chromosomal site via site-specific recombination.

Figure 1B:
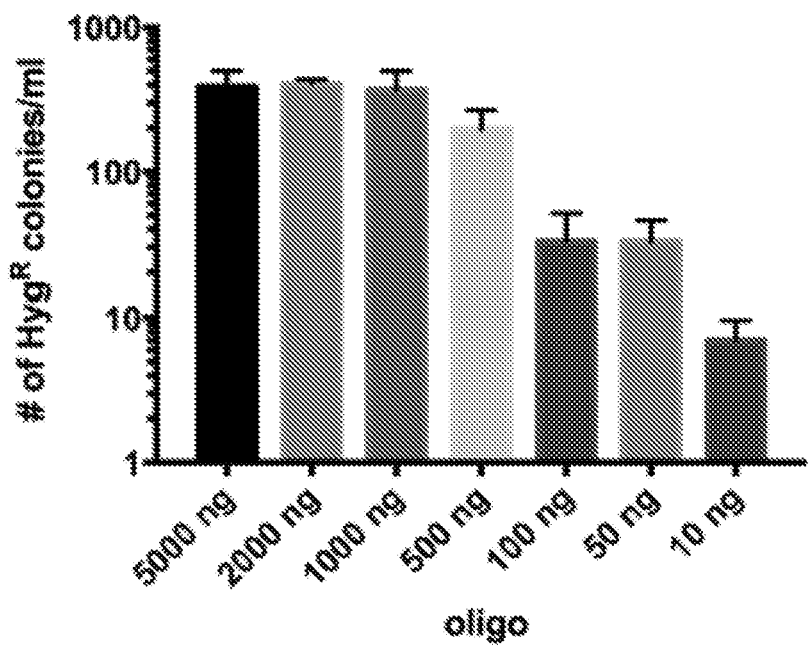

An assay was designed to measure the frequency of incorporation of an oligo containing an insertion of approximately the size of a 48 bp attP site into the mycobacterial chromosome (FIG. 1A). For this purpose, a hygromycin resistance gene, with an internal 60 bp deletion, was integrated into the L5 phage attachment site of the *M. smegmatis* chromosome. Oligos (180-mers) targeting the lagging strand template of the impaired Hyg$^R$ marker and containing the missing 60 bases (as well as 60 bases flanking the deletion site) were electroporated into *M. smegmatis* expressing the Che9c RecT annealase from the anhydrotetracycline (ATc)-inducible Ptet promoter (pKM402). The frequency of oligo incorporation was determined as the number of Hyg$^R$ transformants among the survivors of electroporation. The number of Hyg$^R$ transformants generated varied from less than 10 to over 300, depending on the amount of oligo used (FIG. 1B). At about 1 μg of oligo, the total number of Hyg$^R$ recombinants plateaued at approximately 350 transformants per electroporation, which corresponds to a frequency of $2 \times 10^{-6}$ recombinants per survivor of electroporation. In an experiment where the target contained a 1 bp change creating a premature stop codon in the hyg-resistance gene, a 60 base oligo was used to restore Hyg resistance at a frequency of $4 \times 10^{-4}$ recombinants per survivor of electroporation. Thus, the RecT annealase is capable of integrating an oligo that contains a 60 base insertion into the mycobacterial chromosome, albeit at a frequency which is ~500-fold lower relative to a single base pair change.

Example 3: Development of ORBIT

To convert the recombineering of an oligo into a selectable event, co-electroporation of the attP-containing oligo with an attB-containing non-replicating vector (Hyg$^R$) into a cell that expresses both the RecT annealase and the phage Bxb1 Integrase, which would allow both homologous and site-specific recombination events to occur within the same outgrowth period, was investigated. Since the oligo is designed to direct the integration of the genetic information contained in the non-replicating plasmid, these elements were termed, "targeting oligo" and "payload plasmid".

Figure 2B:
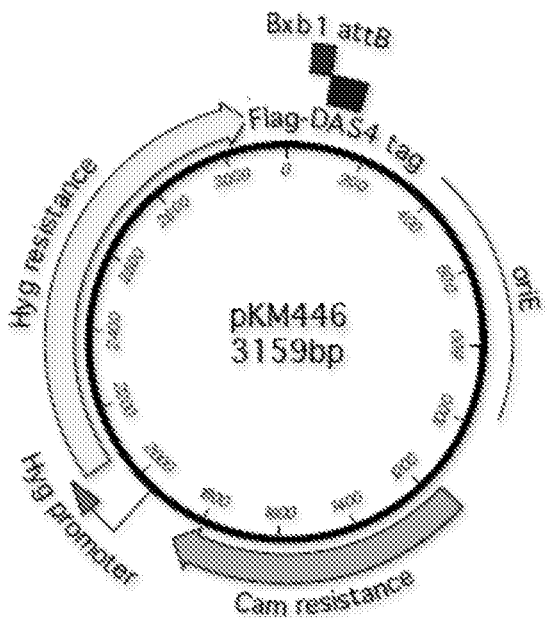

Two plasmids were generated to test this methodology (FIGS. 2A-2B). pKM444 produces the recombination functions. This mycobacterial shuttle vector expresses both the Che9c phage RecT annealase and the Bxb1 phage integrase (Int) from the Ptet promoter (FIG. 2A). pKM446 is a payload plasmid that will not replicate in mycobacteria. This vector encodes a hyg resistance marker for selection in mycobacteria and a Bxb1 attB site (FIG. 2B). Adjacent to the attB site is a sequence encoding both a FLAG tag and a DAS+4 peptide tag designed to be in frame with a targeted chromosomal gene following integration of the plasmid. The DAS+4 tag directs a fusion protein for degradation via the ClpXP system upon expression of the SspB adapter protein. Targeting oligos were designed to direct the integration of attP to the 3' ends of the *M. smegmatis* recA, DivIVA and leuB genes, just in front of the stop codon. A site-specific recombination event between the inserted attP and the co-electroporated pKM446 would then generate a DAS+4 fusion to these target genes. The oligos used in this example are as follows:

```
recA
                                      (SEQ ID NO: 4)
GACGTTCTTGGCCTGCTCCTCACGGGTGCGAGGATCCTGCGCCTGCTCGC

CGTCGGGGACGTCCGACGGCTCAGGTTTGTACCGTACACCACTGAGACCG

CGGTGGTTGACCAGACAAACCGAAGTCAACCGGGGCCGGGAGGACGTCAT

CGGCTTCAGCGGTCACGACGGCGCCGATACCGAGCTTCTCT leuB
                                      (SEQ ID NO: 5)
CAGTGGCCGAGACAGCACTGAGTGGCGCACAGGCCGGAAAGCCTGTGCGC

CTTCGACGCGAAAACTCCTAGGTTTGTACCGTACACCACTGAGACCGCGG

TGGTTGACCAGACAAACCGAGCAGAGAACGGATCCGCTCGCCCACCGCGC

TGGTGGACAGCTTCTCGTCGCCGCGGGTGGCCAGATGC divVIA
                                      (SEQ ID NO: 6)
TCCGACCACGGTGACGGACCCATCGAGTCAGCCCCGGGTCGTGTCGACGC

GGGGCCTGTCGCCGGACGAGTCAGGTTTGTACCGTACACCACTGAGACCG

CGGTGGTTGACCAGACAAACCGTTGTTGCCGCGGTTGAACTGGCCGAATC

CGCTGGCGTCGCTGTTCGCGCTGGAATCGACCGGTGCGGCC
```

These targeting oligos, which anneal to the lagging strand template of the replication fork, were co-electroporated with the pKM446 payload plasmid into *M. smegmatis* that expressed both Che9c RecT annealase and Bxb1 Integrase. Among the Hyg$^R$ colonies resulting from this transformation, 9 out of 12 candidates tested by PCR contained the expected recombination structure, in which pKM446 was inserted between attR and attL sites at the predicted oligo-directed integration site (FIGS. 2C-2E). The fusion of the target genes to the FLAG-DAS+4 degradation tag was verified by sequencing the PCR products of the 5' junctions. The sequence of the recA-Flag-DAS+4 fusion generated by ORBIT is shown below:

```
RecA (C-terminal end)
                                      (SEQ ID NO: 7)
AGAGAAGCTCGGTATCGGCGCCGTCGTGACCGCTGAAGCCGATGACGTC

CTCCCGGCCCCGGTTGACTTC attR (core sequence in bold; underlined "CG"
included to fuse attR to tags)
                                      (SEQ ID NO: 8)
GGTTTGTCTGGTCAACCACCGCGGTCTCCGTCGTCAGGATCATCG FLAG tag
                                      (SEQ ID NO: 9)
GACTACAAGGACGACGACGACAAG DAS + 4 tag (TAG sequence from RecA)
                                      (SEQ ID NO: 10)
GCCGCCAACGACGAGAACTACTCCGAGAACTACGCGGACGCCAGCTAG
```

To test the functionality of the tag and verify that the mutated locus was the only copy of the targeted gene in the cell, the protein degradation system for controlling the expression of DAS+4-tagged proteins in *M. smegmatis* and *M. tuberculosis* was used. In this system, the degradation of the DAS+4 tagged protein is promoted by expression of the *E. coli* SspB protein. Two different sspB expression systems were used, which induce degradation of the target protein either by adding ATc (Tet-OFF) or removing ATc (Tet-ON).

Figure 3:
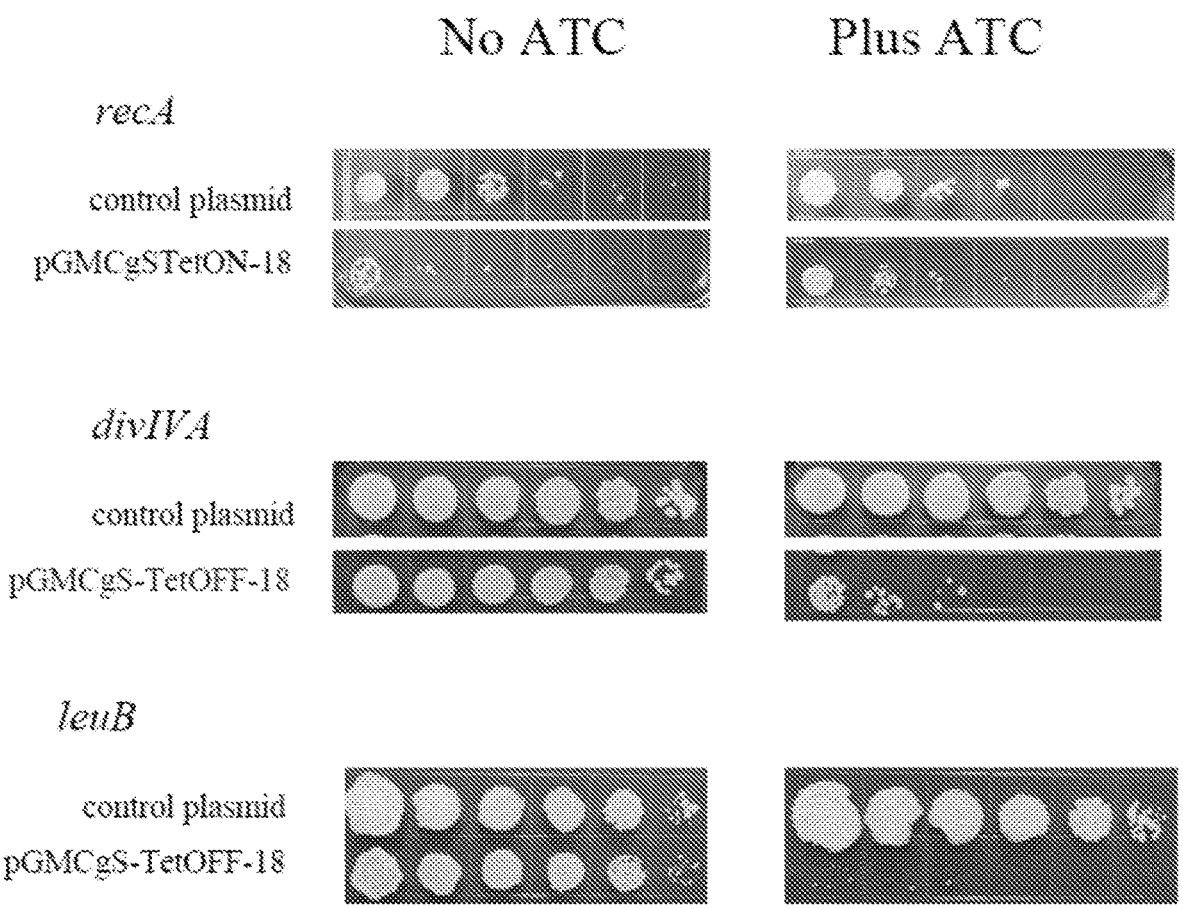
FIG. 3 shows knockdown phenotypes of ORBIT-generated DAS+4-tagged strains. The growth phenotypes of the Flag-DAS+4 tagged strains were analyzed after transformation of an SspB-expressing plasmid.

Cells containing the recA-DAS+4 fusion were transformed with pGMCgS-TETON-18, allowing the induction of SspB in the absence of ATc; RecA function was quantified using a UV resistance assay. When grown in the presence of ATc, the recA-DAS+4-tagged strain containing either the SspB-expressing plasmid or control plasmid showed similar levels of UV sensitivity (FIG. 3). In contrast, the sensitivity of the tagged strain with SspB was enhanced in the absence of ATc (FIG. 3). The divIVA and leuB DAS+4-tagged strains were transformed with pGMCgS-TETOFF-18, which produces SspB upon ATc addition. In both cases, addition of ATc inhibited the growth of these mutants, consistent with the essentiality of these genes on the media used in this study (FIG. 3). The defect of LeuB depletion could be reversed by the addition of leucine to the plates, verifying that that this phenotype was linked to the engineered mutation. Thus, the ORBIT method generates function-altering mutations without the need to construct either target-specific plasmids or long dsDNA recombineering substrates.

Figure 4:
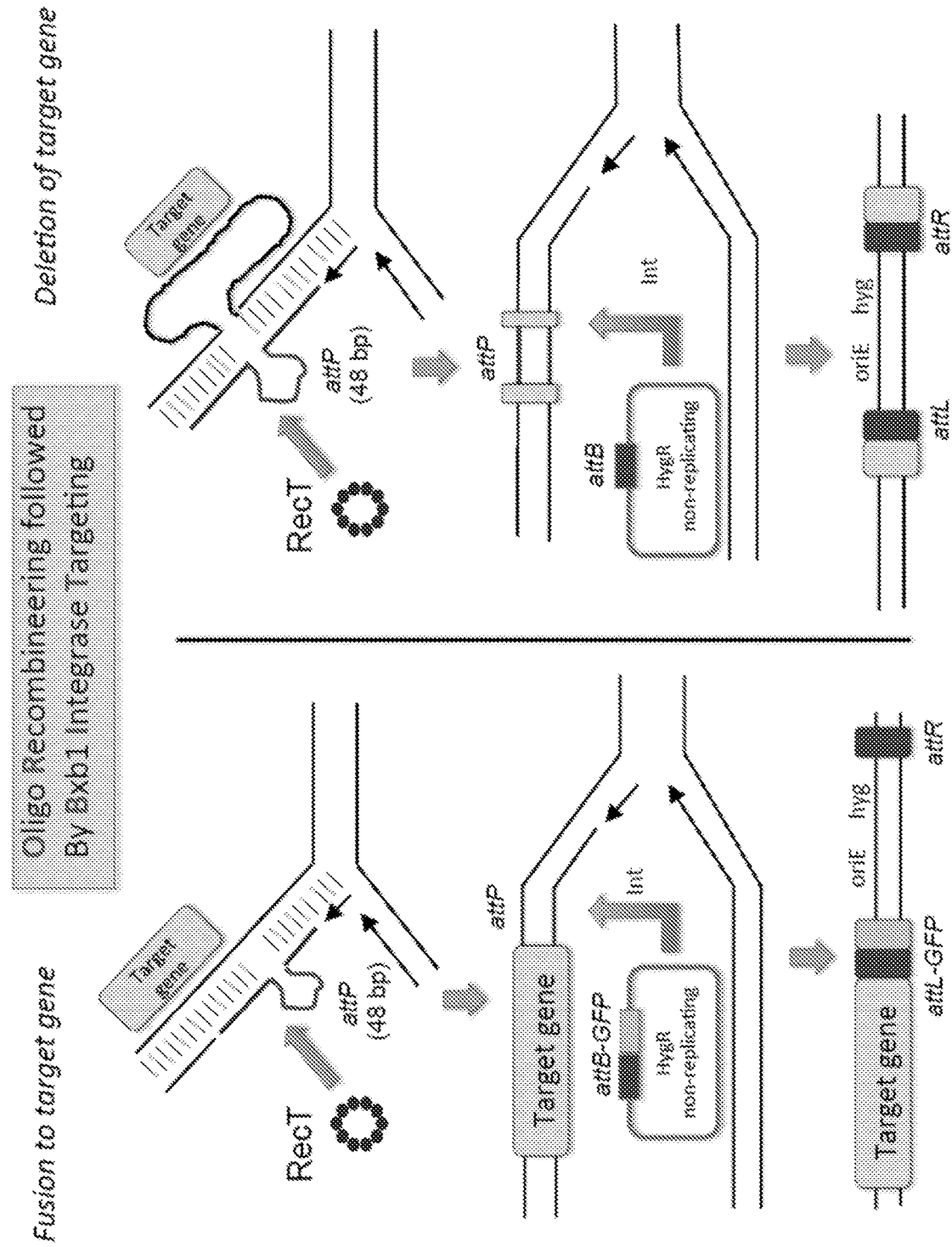
FIG. 4 shows a schematic depiction of ORBIT-promoted gene alteration. The site of action occurs at the replication fork. An oligomer containing a single-stranded version of the Bxb1 attP site (top pictures) was co-electroporated with an attB-containing non-replicating plasmid into a mycobacterial host cell expressing both RecT annealase and Bxb1 Integrase. RecT promotes annealing of the oligo to the lagging strand template. Following DNA replication through this region, an attP site was formed in the chromosome (middle pictures). In the same outgrowth period, Bxb1 Integrase promoted site-specific insertion of the plasmid into the chromosome (attBxattP). Left side: The oligo is designed so that attP was inserted just before the stop codon. The integration event fused the GFP tag in-frame to the C-terminal end of the target gene (with an attL site in-frame between them); the recombinant is selected for by Hyg$^R$. Right side: The oligo is designed so that attP replaces the target gene and the plasmid integration event allows hygromycin resistance to be used to select for the knockout.

The scheme of using both RecT and Bxb1 Integrase simultaneously to promote modification of a chromosomal target gene is diagrammed in FIG. 4; the process is called ORBIT (for Oligo-mediated Recombineering followed by Bxb1 Integrase Targeting). In some embodiments, targeting oligos are designed to delete a portion of the chromosome during the ORBIT reaction (FIG. 4, right side) to create deletions.

Figure 5A:
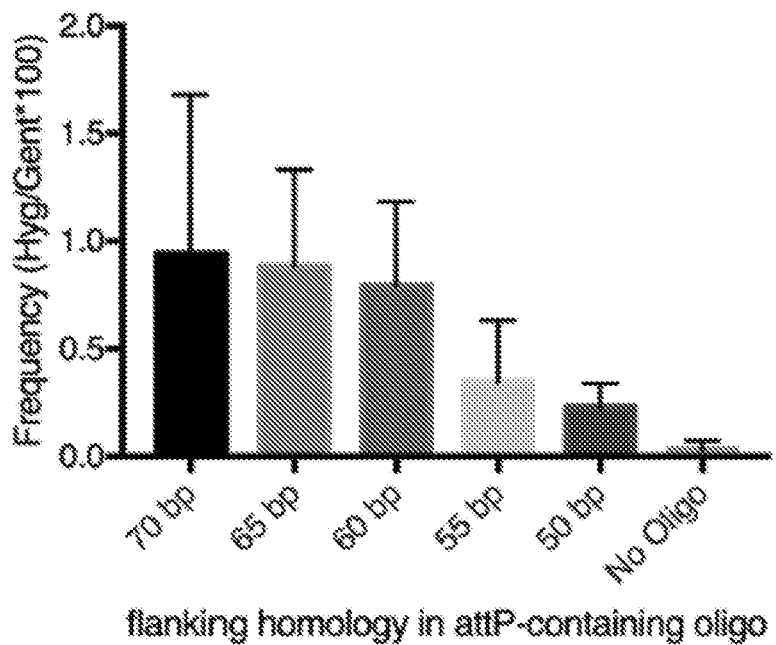
FIGS. 5A-5B show data relating to parameters of the ORBIT process.

Two features of ORBIT that were investigated are the length of the homologous arms (HAs) in the targeting oligo, and the relative amounts of oligo and non-replicating plasmid used for co-electroporation. The HAs of a polA-targeting oligo, were varied from 50 to 70 bases (oligo lengths, including attP, were from 148 to 188 bases). The oligos were mixed with 200 ng of pKM446 and transformed into *M. smegmatis* containing pKM444. While there is variability in the number of Hyg-resistant transformants from each electroporation, oligos containing longer HAs produced more transformants (FIG. 5A). Below 40 base pair HAs, no $Hyg^R$ transformants were observed above the number seen in the no oligo control.

Figure 5B:
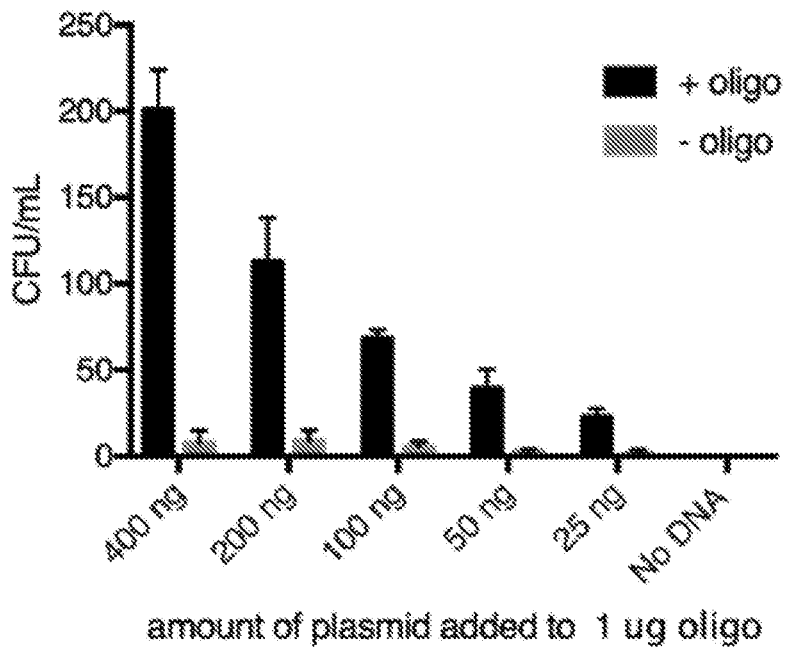

The ratio of oligo to plasmid was also investigated. A concentration of 1 µg targeting oligo was co-electroporated with various amounts of the payload plasmid pKM446. More $Hyg^R$ transformants were observed when more plasmid is used, but there was also a small increase in the number of oligo-independent transformants that presumably represent illegitimate recombinants (FIG. 5B). PCR screening confirmed that 39/40 Hyg-resistant transformants recovered in this experiment (using 8 candidates of each transformation), represented the desired oligo-directed recombination events. Generally, 1 µg of oligo was combined with 200 ng of plasmid in the transformations described below.

Example 4: ORBIT-Promoted Knockdowns and Knockouts in *M. smegmatis* and *M. tuberculosis*

Figure 6A:
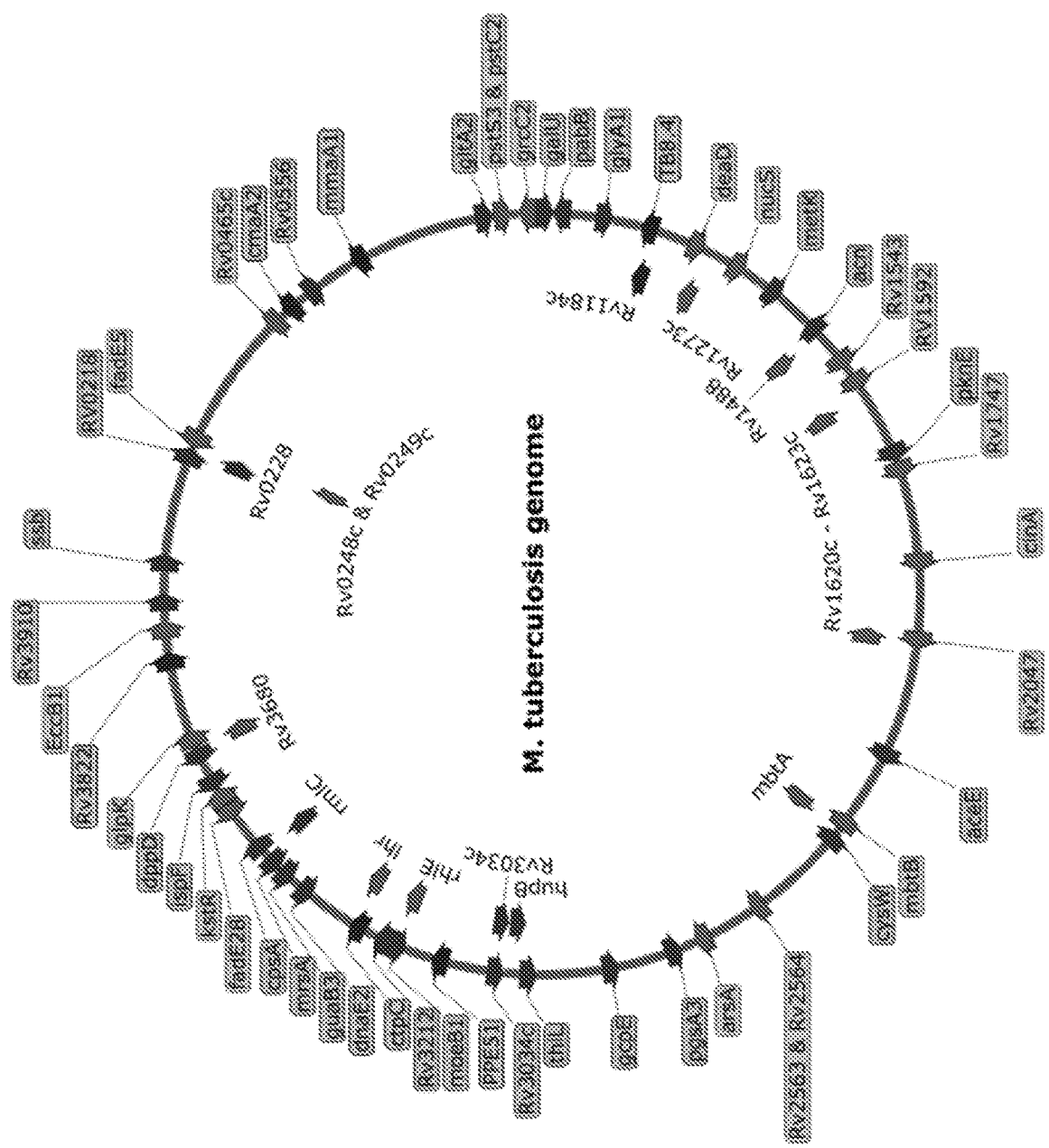
FIGS. 6A-6B show schematics depicting examples of ORBIT-generated insertions and deletions in *M. tuberculosis* and *M. smegmatis*. Target gene deletions and tags were placed at a variety of positions in the chromosomes of both *M. tuberculosis* (FIG. 6A) and *M. smegmatis* (FIG. 6B). In most cases, the oligos contained an attP site flanked by 70 bases of target homology. Insertions (either DAS+4, GFP or His-Flag) and deletions are shown. A description of all the types of modifications performed by ORBIT are shown in Table 1 (for *M. smegmatis*) and Table 2 (for *M. tuberculosis*).
Figure 6B:
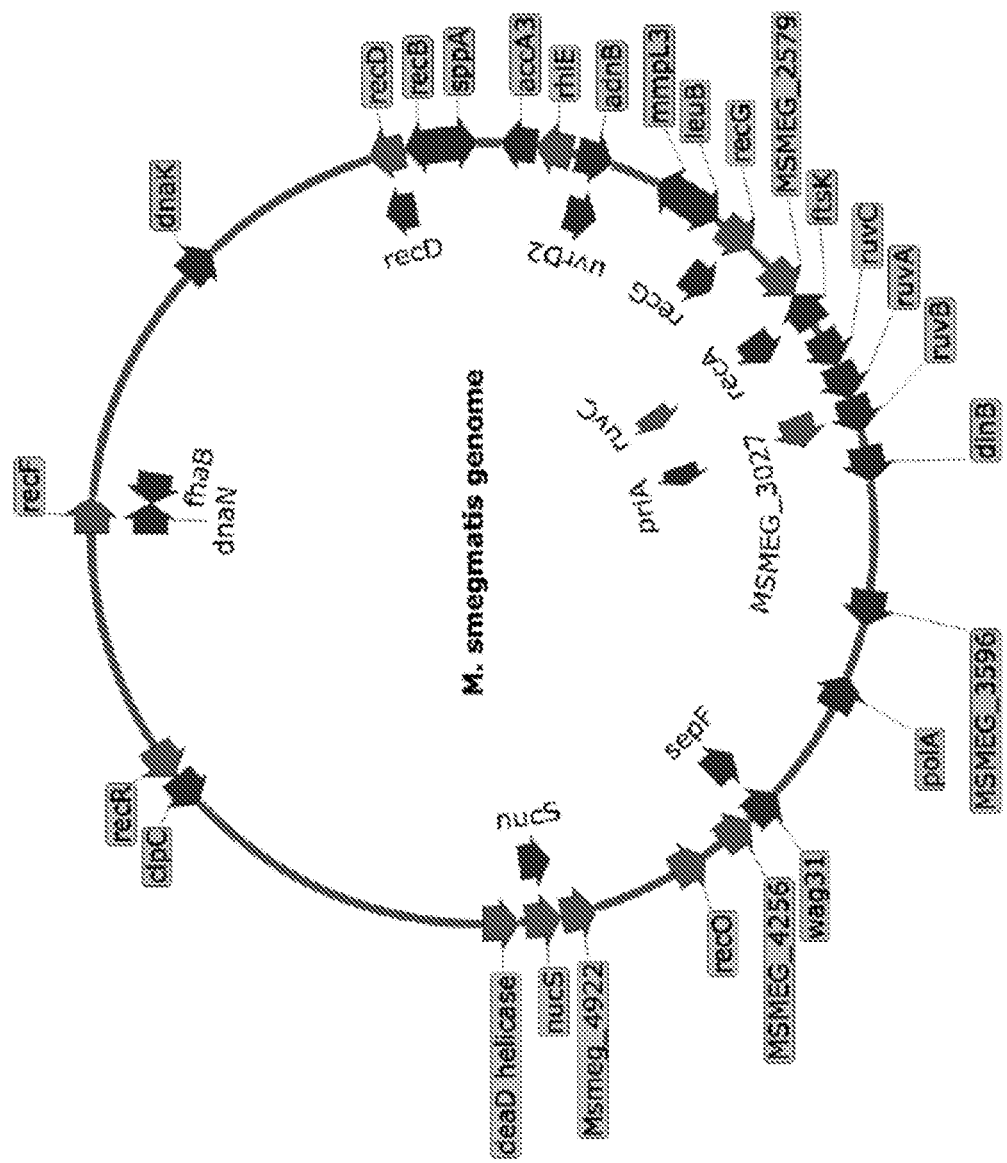

To determine if ORBIT-promoted modifications could be generally engineered throughout the chromosome, a variety of genes in *M. tuberculosis* and *M. smegmatis* were targeted. For C-terminal tags, the attP site was placed just in front of the stop codon of the target gene. For knockouts, the attP site was flanked by 60-70 bases, which included the first and last 10 codons of the target gene (including the start and termination codons), which generally results in the deletion of intervening chromosomal sequence. Overall, over 100 strains were produced where the target genes have either been deleted or C-terminally tagged (see FIGS. 6A-6B and Tables 1 & 2). For most of these targets, between 5 to 50 colonies were typically seen after plating 0.5 ml of the overnight outgrowth. Usually, only 2-4 $Hyg^R$ candidates needed to be analyzed by PCR to identify at least one strain that contained the payload plasmid in the site designated by the targeting oligo. Most of the targeting oligos used for these genomic modifications contained either 60 or 70 bases of flanking homology. An oligo targeting the aceE gene containing only 45 bases homology on each side of attP also produced the desired recombinant in 4 of 6 clones. However, lowering flanking homologies below 40 bases decreased the percentage of correct recombinants dramatically, largely as a result of an increased number of illegitimate recombination events.

In order to cure recombinants of the RecT-Int producing plasmid following modification, a SacB-containing derivative of pKM444 was constructed (pKM461). A number of genes were tagged in a pKM461-bearing strain (including recG, dnaN and ftsK), then plated directly on Hyg-sucrose plates to both select for the recombinant and to cure the strain of the RecT-Int producer. This process was observed to produce fewer colonies than previously observed with pKM444, but can rapidly produce plasmid-free mutants.

Genetic modifications with ORBIT were observed to be stable. An excision event promoted by the Bxb1 SSR system generally requires an additional factor called gp47, which is not present in the hosts used for these experiments. The stability of ORBIT-mediated modifications was verified by observing that the integrated payload plasmid, in a number of *M. smegmatis* mutants generated in this example, was not lost after more than 100 generations of growth in the absence of drug selection.

Example 5: Library Production

In order to expand the types of modifications that can be made via ORBIT, a set of payload plasmids all containing the Bxb1 attB site fused to different types of tags was produced. In addition to the Flag-DAS+4 plasmids, plasmids were produced to create C-terminal targeted fusions with combinations of eGFP, mVenus, SNAP, CLIP, Myc and His epitopes, and TEV cleavage sites. These tags facilitate both protein localization by fluorescence and tandem affinity purification (Table 3). In addition, plasmids to generate chromosomal knockouts and promoter replacements using either hygromycin- or zeocin-resistance as a selection for the recombinant were produced (see Table 3). Generally, any number of payload plasmids can be matched with a single targeting oligo to generate a variety of functional gene modifications.

As with any chromosomal engineering method, the effect of the modification on expression of downstream functions must be considered, especially if the target gene is within an operon. The ORBIT knockout plasmid pKM464 was designed so that once integrated, the hyg gene is positioned at the junction of the insertion site allowing downstream genes to be transcribed by the hyg promoter. This is generally sufficient for the generation of most mutations (see Table 1). For additional options, variants of pKM446 (for Flag-DAS+4 tags) pKM464 (for knockouts) were designed that contain a second promoter ($P_{GroEL}$) to drive higher transcription downstream of the insertion site, if needed (Table 3). Similar plasmids can be generated with promoters of varying strengths, as needed.

Figure 7:
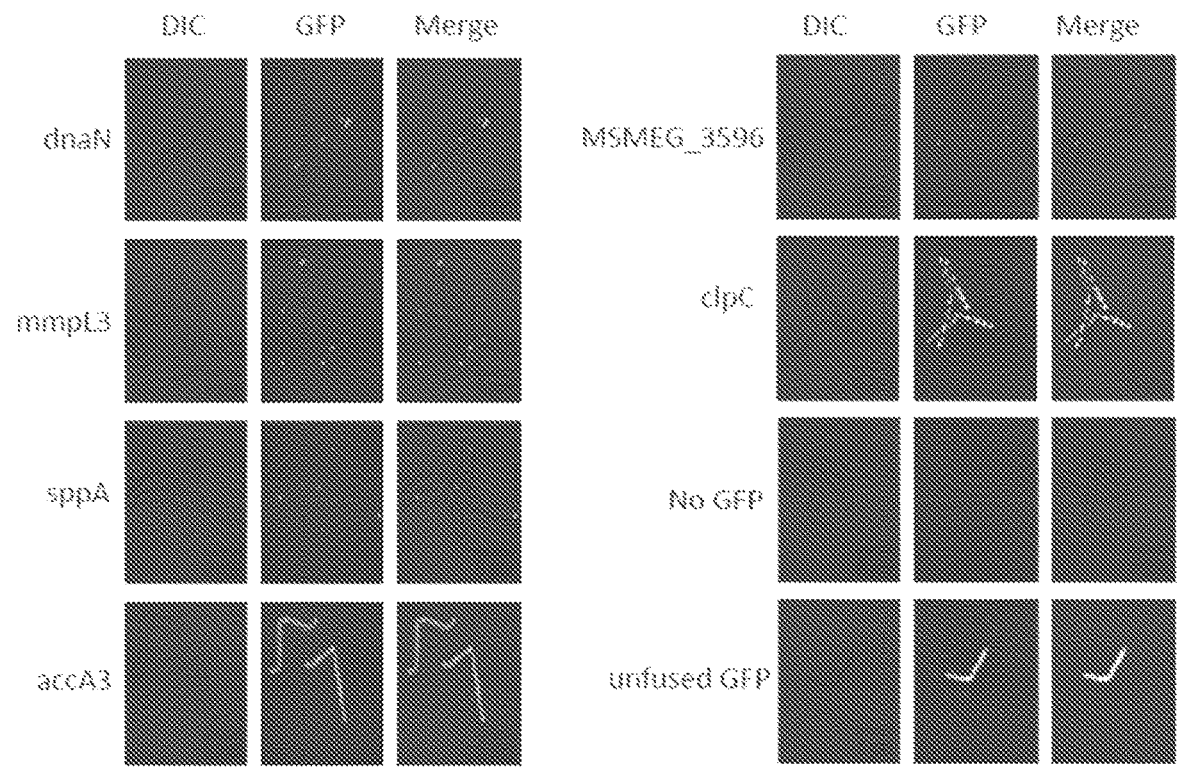
FIG. 7 shows images of ORBIT-generated GFP fusions. *M. smegmatis* cells containing EFP-tagged targets were grown in 7H9-AD-tween to an optical density of 0.8. One microliter of the culture was used to prepare the slide for the microscope. Each bacterial strain was imaged using differential interference contrast (DIC) and GFP channels.

To demonstrate the functionality of these additional tags, ORBIT was used to construct eGFP fusions with a number of *M. smegmatis* genes. AccA3 (a protein involved in cell wall synthesis), MmpL3 (the essential mycolate transporter suspected to reside at the pole), DnaN (the beta subunit of DNA polymerase III), known to be located in discrete cytoplasmic foci, and three genes with unknown distribution patterns were fused to tags. The eGFP payload plasmid pKM468 (Table 3) was used to tag each gene in situ at the endogenous chromosomal locus. MmpL3-eGFP, and DnaN-eGFP was found at both the cell poles and along the cell body walls (FIG. 7). For DnaN-GFP, the punctate spots identifies positions of the replication forks and are shown as occurring in non-polar regions of the cell (see FIG. 7), in accordance with previous observations. Chromosomally expressed AccA3-eGFP was found both at the poles and other position on the cell body. eGFP-tagged alleles of MSMEG_3596, SppA and ClpC were all found at distinct sites, which were distinct from the diffuse cytosolic distribution of unfused eGFP. Overall, ORBIT is an efficient way to tag native genes in the chromosome with different types of tags without having to create target- and modification-specific dsDNA recombination substrates. Also, by expressing each gene at its native level, aberrant localization or complex formation due to overexpression can be avoided.

One can also integrate attB-containing ORBIT plasmids to change the endogenous levels of expression of a chromosomal gene. A series of ORBIT plasmids containing promoters of different strengths that can be used to drive the expression of genes downstream of the plasmid insertion site were produced (see Table 3). For use of these plasmids, the ORBIT oligo is designed to replace the endogenous promoter with attP. The target gene's ribosome binding site, if recognized, can also be deleted, replaced, or left intact, depending on the final level of expression desired. To test this scheme, ORBIT was performed in an *M. smegmatis* strain where a chromosomal lacZ gene is under control of the mycobacterial PAg85 promoter containing a weak ribosome binding site.

Figure 8A:
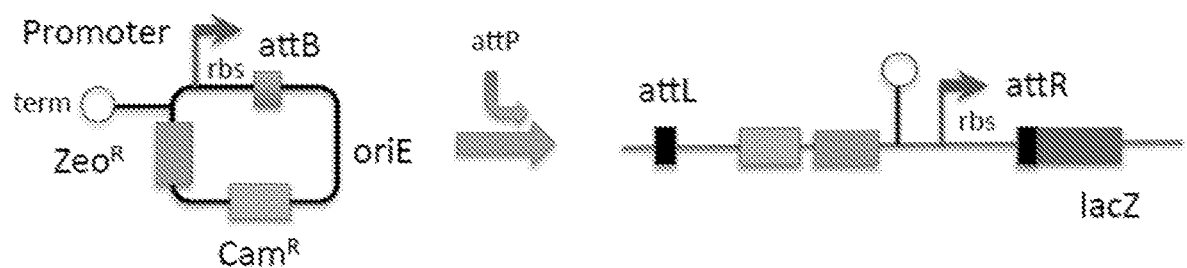
FIGS. 8A-8B show examples of promoter replacement by ORBIT.
Figure 8B:
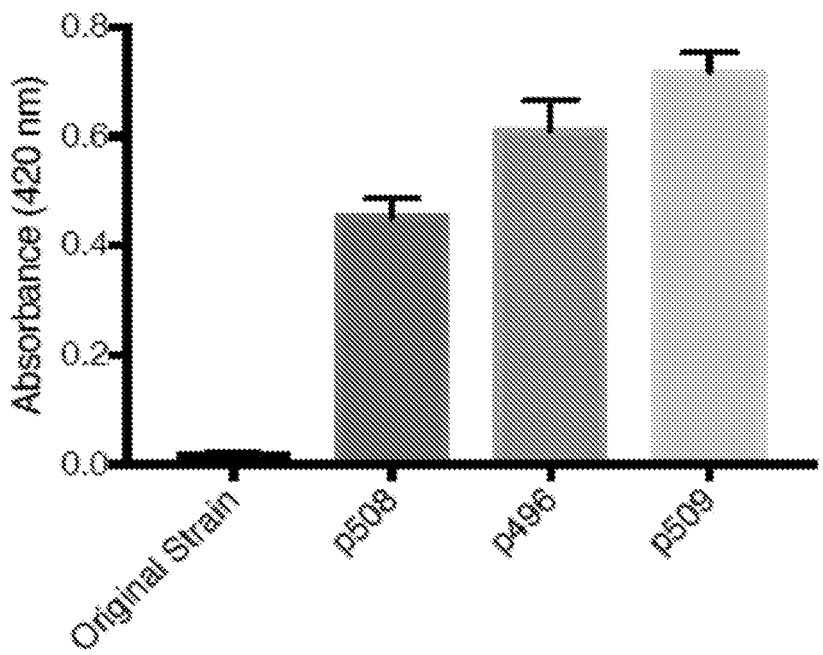

ORBIT was used to replace PAg85 with one of three different promoters: $P_{imyc}$, $P_{GroEL}$ or P38. Plasmids containing these promoters are listed according to increasing strengths of expression. The promoters were transferred to ORBIT integration plasmids and placed upstream of the Bxb1 attB site (see FIG. 8A). An optimized ribosome binding sites (rbs: AGAAAGGAGGAAGGA (SEQ ID NO: 11)) was included between the promoters and the attB site to increase the overall expression of β-galactosidase relative to the starting strain, where an endogenous Shine-Delgarno sequence could not be recognized. ORBIT recombinants were identified by resistance to zeocin and verified by chromosomal PCR analysis as described above. As seen in FIG. 8B, the total amount of β-galactosidase in each extract increased in accordance with the listed strengths of the three promoters used in these assays. Thus, endogenous promoters can be altered using ORBIT to express different levels of a target gene.

Example 6: Markerless Gene Deletions

The ORBIT protocol represents a unique way to construct markerless gene deletions in a process involving reversal of plasmid integration step. The Bxb1 phage produces gp47 protein, which has been shown to be a recombination directionality factor (RDF). Along with the Bxb1 integrase, gp47 acts to promote site-specific recombination between attL and attR, restoring the attP site. By replacing recT with gp47 in pKM461 and exchanging the Hyg$^r$ gene with a Zeo$^r$ cassette (ble), a plasmid was generated that expresses both gp47 and integrase under the control of Ptet (pKM512). The *M. smegmatis* ORBIT-generated deletion strain ΔMSMEG_4392, not yet cured of the Kan$^r$ plasmid pKM461, was transformed with pKM512 (Zeo$^r$), grown in the presence of anhydrotetracycline (ATc), and plated on 7H10-sucrose plates as described above. Of 37 colonies of strain ΔMSMEG_4392 treated in this manner, 7 were sensitive to hygromycin; in addition, all of them were sensitive to both kanamycin and zeocin. Site-specific recombination between the attR and attL sites replaced the deleted portion of MSMEG_4392 with the attP site, creating an in-frame deletion, which was verified by sequencing in 4 of the 7 HygS colonies described above. Thus, mutants of mycobacteria devoid of any antibiotic resistance can be generated following construction of ORBIT-generated deletions.

TABLE 1

ORBIT-promoted *M. smegmatis* modifications

| Gene | | Function | # correct/# tested |
|---|---|---|---|
| Flag-Das4 tags: | | | |
| leuB | MSMEG_2379 | 3-isopropylmalate dehydrogenase | 2/4 |
| recA | MSMEG_2723 | recombinase | 4/4 |
| wag31 | MSMEG_4217 | DivIVA protein | 3/4 |
| dnaN | MSMEG_0001 | DNA polymerase III, beta subunit | 2/2 |
| dinB | MSMEG_3172 | DNA gyrase | 2/2 |
| dnaK | MSMEG_0709 | chaperone (heat shock) | 1/2 |
| recD | MSMEG_1325 | ExoV, a-subunit | 2/4 |
| recB | MSMEG_1327 | ExoV, b-subunit | 2/2 |
| adnB | MSMEG_1943 | ATP dependent helicase/recombinase | 2/2 |
| dnaE2 | MSMEG_1633 | DNA polymerase III, alpha subunit | 0/2 |
| recG | MSMEG_2403 | ATP-dependent DNA helicase | 2/2 |
| ftsK | MSMEG_2690 | DNA translocase | 3/6 |
| ruvA | MSMEG_2944 | Holliday junction branch migration | 1/2 |
| ruvB | MSMEG_2945 | Holliday junction branch migration | 3/4 |
| ruvC | MSMEG_2943 | Holliday junction resolvase | 1/2 |
| priA | MSMEG_3061 | replication restart | 2/2 |
| polA | MSMEG_3839 | DNA polymerase I | 4/6 |
| dinB | MSMEG_3172 | DNA polymerase IV | 2/2 |
| fhaB | MSMEG_0034 | FHA domain-containing protein | 6/12 |
| sepF | MSMEG_4219 | Interacts with FtsZ and MurG | 1/2 |

TABLE 1-continued

ORBIT-promoted M. smegmatis modifications

| Gene | | Function | # correct/# tested |
|---|---|---|---|
| uvrD2 | MSMEG_1952 | ATP-dependent DNA helicase | 2/2 |
| nucS | MSMEG_4493 | ssDNA binding protein | 3/4 |
| — | MSMEG_4922 | conserved hypothetical protein | 3/4 |
| GFP tags: | | | |
| dnaN | MSMEG_0001 | | nr |
| mmpL3 | MSMEG_0205 | MmpL family protein | nr |
| sppA | MSMEG_1476 | signal peptide peptidase | nr |
| AccA3 | MSMEG_1807 | acetyl-/propionyl-coenzyme A carboxylase alpha chain | nr |
| clpC | MSMEG_6091 | ATP-dependent protease ATP-binding protein | nr |
| — | MSMEG_3596 | ATPase | nr |
| Deletions: | | | |
| ΔrecD | MSMEG_1325 | ExoV, a-subunit | 2/4 |
| ΔrecF | MSMEG_0003 | Replication repair protein | 2/4 |
| ΔrecG | MSMEG_2403 | ATP-dependent DNA helicase | 2/2 |
| ΔrecO | MSMEG_4491 | DNA repair protein | 1/2 |
| ΔruvC | MSMEG_2943 | Holliday junction resolvase | 2/6 |
| ΔrecR | MSMEG_6279 | Recombination protein | 4/6 |
| ΔnusS | MSMEG_4923 | mismatch repair function | nr |
| — | MSMEG_4922 | conserved hypothetical protein | nr |
| ΔrhlE | MSMEG_1930 | RNA helicase | nr |
| ΔdeadD | MSMEG_5042 | deaD RNA helicase | nr |
| — | MSMEG_2579 | unknown | nr |
| — | MSMEG_3027 | unknown | nr |
| — | MSMEG_4256 | NLP/P60 family protein | nr |

TABLE 2

ORBIT-promoted M. tuberculosis modifications

| RV# | Gene | Function |
|---|---|---|
| Knockouts: | | |
| Rv0503c | cmaA2 | Cyclopropane-fatty-acyl-phospholipid synthase |
| Rv0645c | mmaA1 | Methoxy mycolic acid synthase |
| Rv1174c | TB8.4 | Low molecular weight T-cell antigen TB8.4 |
| Rv1184c | Rv1184c | Possible exported protein |
| Rv1273c | Rv1273c | Probable drugs-transport transmembrane ABC transporter |
| Rv1901 | cinA | Probable CinA-like protein CinA |
| Rv3136 | PPE51 | PPE family protein PPE51 |
| Rv3822 | Rv3822 | Conserved hypothetical protein |
| Rv1747 | Rv1747 | Probable conserved transmembrane ABC transporter |
| Rv0248c | Rv0248c | Probable succinate dehydrogenase |
| Rv0249c | Rv0249c | Probable succinate dehydrogenase |
| Rv3696 | glpK | Probable glycerol kinase |
| Rv1543 | Rv1543 | Possible fatty acyl-CoA reductase |
| Rv1621c | CydD | transmembrane ATP-binding protein ABC transporter CydD |
| Rv1623c | CydA | Probable integral membrane cytochrome D ubiquinol oxidase |
| Rv2048c | Pks12 | Polyketide synthase |
| Rv2684 | arsA | Probable arsenic-transport integral membrane protein ArsA |
| Rv3680 | Rv3680 | Probable anion transporter ATPase |
| Rv2047 | Rv2047 | Conserved hypothetical protein |
| Rv0244c | FadE5 | Probable acyl-CoA dehydrogenase FadE5 |
| Rv1488 | Rv1488 | Possible exported conserved protein |
| Rv1161-1164 | NarG- NarI | Nitrate reduction |
| Rv0465c | Rv0465c | Probable transcriptional regulatory protein |
| Rv1620c-1623c | cyd operon | Respiratory chain |
| Rv2384 | mbtA | salicyl-AMP ligase (SAL-AMP ligase) + salicyl-S-ArCP synthetase |
| Rv2383c | mbtB | phenyloxazoline synthetase |
| Rv3283 | sseA | Probable thiosulfate sulfurtransferase SseA |
| Rv3270 | ctpC | Probable metal cation-transporting P-type ATPase C |
| Rv0928 | pstS3 | Periplasmic phosphate-binding lipoprotein PstS3 |
| Rv0929 | pstC2 | Phosphate-transport integral membrane protein ABC transporter |
| Rv3869 | EccB1 | ESX-1 type VII secretion system protein |
| Rv2563 | Rv2563 | glutamine-transport transmembrane protein ABC transporter |
| Rv2564 | Rv2564 | glutamine-transport ATP-binding protein ABC transporter |
| Rv3544c | fadE28 | Probable acyl-CoA dehydrogenase |
| Rv3574 | kstR | Transcriptional regulatory protein |

TABLE 2-continued

ORBIT-promoted M. tuberculosis modifications

| RV# | Gene | Function |
|---|---|---|
| Rv1321 | nucS | Probable mismatch repair protein |
| Rv3211 | rhlE | Probable ATP-dependent RNA helicase |
| Rv3296 | lhr | Probable ATP-dep. helicase Lhr (large helicase-related protein) |
| Rv1253 | deaD | Probable cold-shock DeaD-box protein A homolog |
| Rv0989c | grcC2 | Probable polyprenyl-diphosphate synthase |
| Rv1592 | Rv1592 | Conserved hypothetical protein |
| Insertions (Flag-Das4 tags: | | |
| Rv2241 | aceE | Pyruvate dehydrogenase E1 component |
| Rv0218 | Rv0218 | Probable conserved transmembrane protein |
| Rv3370c | dnaE2 | DNA polymerase III (alpha chain) |
| Rv1475c | acn | Probable iron-regulated aconitate hydratase |
| Rv3663c | dppD | Probable dipeptide-transport ATP-binding protein |
| Rv1743 | pknE | Probable transmembrane serine/threonine-protein kinase E |
| Rv0228 | Rv0228 | Probable integral membrane acyltransferase |
| Rv1005c | pabB | Probable para-aminobenzoate synthase component |
| Rv0556 | Rv0556 | Probable conserved transmembrane protein |
| rv0993 | galU | UTP--glucose-1-phosphate uridylyltransferase GalU |
| Rv3465 | rmlC | dTDP-4-dehydrorhamnose 3,5-epimerase |
| Rv3034c | Rv3034c | Possible transferase |
| Rv1093 | glyA1 | Serine hydroxymethyltransferase |
| Rv2398c | cysW | Probable sulfate-transport membrane protein ABC transporter |
| Rv0054 | ssb | Single-strand binding protein |
| Rv3206c | moeB1 | Probable molybdenum cofactor biosynthesis protein MoeB1 |
| Rv2977c | thiL | Probable thiamine-monophosphate kinase |
| Rv3910 | Rv3910 | Probable conserved transmembrane protein |
| Rv3441c | mrsA | Probable phospho-sugar mutase |
| Rv2868c | gcpE | Probable GcpE protein |
| Rv3410c | guaB3 | Probable inosine-5'-monophosphate dehydrogenase |
| Rv2746c | pgsA3 | Probable PGP synthase PgsA3 |
| Rv1392 | metK | Probable S-adenosylmethionine synthetase |
| Rv3034c | Rv3034c | Possible transferase |
| Rv3484 | cpsA | Possible conserved protein CpsA |
| Rv0896 | gltA2 | Probable citrate synthase |
| RV2986c | hupB | DNA-binding protein HU homolog |
| Rv3581c | ispF | Probable 2C-methyl-D-erythritol 2,4-cyclodiphosphate synthase |
| Rv3212 | — | Conserved alanine valine rich protein |

TABLE 3

ORBIT integration plasmids

| Plasmid name | Type of Modification | Drug resistance markers |
|---|---|---|
| C-terminal tags: | | |
| pKM446 | C-terminal tag: Flag-DAS tag | $Hyg^R$ |
| pKM468 | C-terminal tag: EGFP-4xGly-TEV-Flag-6xHis | $Hyg^R$ |
| pKM469 | C-terminal tag: Venus-4xGly-TEV-Flag-6xHis | $Hyg^R$ |
| pKM489 | C terminal tag: SNAP tag | $Hyg^R$ |
| pKM490 | C-terminal tag: CLIP tag | $Hyg^R$ |
| pKM491 | C-terminal tag: 4xGly-TEV-Flag-6xHis | $Hyg^R$ |
| pKM492 | C-terminal tag: 4xGly-TEV-Myc-6xHis | $Hyg^R$ |
| pKM493 | C-terminal tag: TEV-Flag-4xGly-EGFP | $Hyg^R$ |
| pKM495 | C-terminal tag: Flag-DAS tag | $Zeo^R$ |
| Knockouts: | | |
| pKM464 | knockout | $Hyg^R$ |
| pKM496 | knockout | $Zeo^R$ |
| Promoter replacements: | | |
| pKM464 | Replace endogenous promoter with $P_{Hyg}$ | $Hyg^R$ |
| pKM496 | Replace endogenous promoter with $P_{GroEL}$ (op-rbs) | $Zeo^R$ |
| pKM508 | Replace endogenous promoter with P21 (op-rbs) | $Zeo^R$ |
| pKM509 | Replace endogenous promoter with P38 (op-rbs) | $Zeo^R$ |

TABLE 4

ORBIT-testing and promotion plasmids

| Plasmid | Functions | Drug resistance marker |
|---|---|---|
| pKM433 | Phage L5 integrating vector; Hyg□60 bp internal deletion; oriE | $Zeo^R$ |
| pKM444 | $P_{Tet}$-Che9c RecT-Bxb1 Int; TetR, oriE, oriM | $Kan^R$ |
| pKM461 | $P_{Tet}$-Che9c RecT-Bxb1 Int; SacRB; TetR, oriE, oriM | $Kan^R$ |

TABLE 5

Examples of targeting oligonucleotides

| Oligo Name | | Sequence | SEQ ID NO: |
|---|---|---|---|
| Rv0054 | ssb | gggcgccgcttgctggacttggccatgagtgtctatctttccgtttcttgatt tgcagttcttggggtcaGGTTTGTACCGTACACCACTG AGACCGCGGTGGTTGACCAGACAAACCgaatg gcggttcgtcatcgccgccgaacgaacccgacgccggtgcgctgc cccacgggtcatctccc | 12 |
| Rv0218 | Rv0218 | catcgccagcaggtgcaatggacctgacccgtaggagtttttgaaacgc gttgcaatgtcgaacatttcaGGTTTGTACCGTACACCAC TGAGACCGCGGTGGTTGACCAGACAAACCcct cttgtggaattcgatgccagcgacccatttcgtgttgtgcacaccgggca gtgcgggaacgatgatg | 13 |
| Rv0244c | FadE5 | aggtggcactctcaacgaggaggatcggcagtgagccactaccggag caacgtccgtgacGGTTTGTCTGGTCAACCACCGCG GTCTCAGTGGTGTACGGTACAAACCatcatggaa ctcgacgaggccgcgttctgatccttatctgttgactctgcgtccaccgga | 14 |
| Rv0248c | Rv0248c | ccacacccgcatactcgcgctgtacgtcatttagcctctccgtcctggatg ctcggccagctcttcgtcgGGTTTGTACCGTACACCAC TGAGACCGCGGTGGTTGACCAGACAAACCact acgtcgtaggagtgccgctcgacctcaaccataaaacctcgctcagcttc tgaaacgatccttcagc | 15 |
| Rv0249c | Rv0249c | accataaaacctcgctcagcttctgaaacgatccttcagccaataaatctg agatctgtgatgctgccacGGTTTGTACCGTACACCAC TGAGACCGCGGTGGTTGACCAGACAAACCcc gatcgcaggacggttcgccgtgggtgcgctcataatgtgatcctcttcg cgtgttatctcgtcgaa | 16 |
| Rv0465c | Rv0465c | gtcttcacaacacccggtacgctcggttgggtgtccaagacctacgtcgg ctcgcgggtcGGTTTGTCTGGTCAACCACCGCGGT CTCAGTGGTGTACGGTACAAACCgtgtccccgtatc tggtgaaacaactatgaccggtcagaacggccaagtcgcgcgtatct | 17 |
| Rv0503c | cmaA2 | cgatctagtggggaaagtagggtccgttcaatgacgtcacagggcgaca cgacaagcggcGGTTTGTCTGGTCAACCACCGCG GTCTCAGTGGTGTACGGTACAAACCgacgtctgc cagttcactctggtcaaataagggtcagccgaaaaagatgttgcgacgg cc | 18 |
| Rv0556 | Rv0556 | acacacactgtcagcgccggctgtcgaaatggttgcgtagcggcatacg gcgtgcgaactctgctgctcaGGTTTGTACCGTACACCA CTGAGACCGCGGTGGTTGACCAGACAAACCg cccgttgcagacgccgaattttcacgacgttccaaccgcttgtccagcac cgctagcacgaccagcgcg | 19 |
| Rv0645c | mmaA1 | ttgtacggttggcgcgggaggttgtcgcctatggccaagctgagaccata ttacgaagagGGTTTGTCTGGTCAACCACCGCGGT CTCAGTGGTGTACGGTACAAACCaacgtcgcccag ttcaccatgaccaagtagctcgtccgctcatatccgttcctgacctg | 20 |
| Rv0896 | gltA2 | ctggcgagcagacgcaaaagcccctaatacctgccggtttaggggctt ttgcgtctgctcgccggcctaGGTTTGTACCGTACACCA CTGAGACCGCGGTGGTTGACCAGACAAACCc cgcgcgtctatggtgacgtagtcgcgctccgtgtagccggtgtagatctg gcggggccggccgatcttg | 21 |
| Rv0928 | pstS3 | tttaccggctggtcgagcgcctcgatgctcattgagggactcacccgttg accttcccgccggcggattgcGGTTTGTACCGTACACCA CTGAGACCGCGGTGGTTGACCAGACAAACCt acggcggcaccaaatcggttgagtttcaattcagttcctaacggccgacc agctgttttgctcgcagca | 22 |
| Rv0929 | pstC2 | tttaccggctggtcgagcgcctcgatgctcattgagggactcacccgttg accttcccgccggcggattgcGGTTTGTACCGTACACCA CTGAGACCGCGGTGGTTGACCAGACAAACCt acggcggcaccaaatcggttgagtttcaattcagttcctaacggccgacc agctgttttgctcgcagca | 23 |
| Rv0989c | grcC2 | gtgtcaatgttgtgcgcatgcctacggccacgagcatgatcccggcagtc agcctgggtgacccgcaattGGTTTGTCTGGTCAACCA CCGCGGTCTCAGTGGTGTACGGTACAAACCc attgatcgaccacgcgatatctgcgtgcgactagcgacacaccccagca actacctgttgacacaacga | 24 |

TABLE 5-continued

Examples of targeting oligonucleotides

| Oligo Name | | Sequence | SEQ ID NO: |
|---|---|---|---|
| rv0993 | galU | ctttccgtcgagccatggggccgggcatcccccaccccggaaccgtcc gtgccgtatcgtcgccaggctaGGTTTGTACCGTACACC ACTGAGACCGCGGTGGTTGACCAGACAAAC Cctgctctgtcagacccagtcgcgccaccaaccatcgccgcaagtccg ggccgtagtcgtcacgatccaat | 25 |
| Rv1093 | glyA1 | tcgggcgccgccgtgtcgcgcggtgatcggcgctctcgcgcttatcgc gccaacgacaggcccgcgtcaGGTTTGTACCGTACACC ACTGAGACCGCGGTGGTTGACCAGACAAAC Cgcggccgaccagactccactcctcgagcccgtcgtagagcggaaac gccctggccagccgggtcgcccga | 26 |
| Rv1174c | TB8.4 | ggtgcaatagtttggggaaggtgtccataaatgaggctgtcgttgaccgc attgagcgccGGTTTGTCTGGTCAACCACCGCGGT CTCAGTGGTGTACGGTACAAACCtcggttgccggct cctgcaacaactattaagcccatgcgggcccatcccgcgacccggc | 27 |
| Rv1184c | Rv1184c | tcacgcacgcgattctcgatgcagaggcagatgaagcgagtgattgcgg gagcattcgcgGGTTTGTCTGGTCAACCACCGCGG TCTCAGTGGTGTACGGTACAAACCttactgggctcc cccgccttcggcggctaaacactaccgctttgatccgtctgccacggc | 28 |
| Rv1253 | deaD | cgctcgagtccgccctgggcggctctttccttgggcagggtcatccgac gtgtttccgccgtggtttgccGGTTTGTACCGTACACCAC TGAGACCGCGGTGGTTGACCAGACAAACCcg ccgcaggcgaatattccgggaaggccatcaggccgtcaagtttagtggt gacccggccacgcctaccg | 29 |
| Rv1273c | Rv1273c | gcagcatgcgcagtgtgcgacagttacccaatgctcctggccctgctgc gccagcacatcGGTTTGTCTGGTCAACCACCGCGG TCTCAGTGGTGTACGGTACAAACCctgagcgccac ggtcgggggtgtagggtgaccgcgccaccgggcgcacgcccccgtgc cg | 30 |
| Rv1321 | nucS | tttgcggcgccgagccatcgcatcagtttaatcgcgcaactcagaacagc cggtactcgccgctatccatGGTTTGTACCGTACACCAC TGAGACCGCGGTGGTTGACCAGACAAACCct gggcgatgactagacgcacccgactcaccttagagcgcgcaacgacgt tgttccttagagcgtgaccg | 31 |
| Rv1392 | metK | agcagacgcagaatcgcacgcggaagcctttccgcgtgcgattctgcgt ctgctcgcgccctcgacgctaGGTTTGTACCGTACACCA CTGAGACCGCGGTGGTTGACCAGACAAACCg atggcgcgcttgaggtcgtcgaccttgtcgagctgctcccacggtaattc gacgtcggtgcggccgaag | 32 |
| Rv1475c | acn | cggtgaggcggactactaccgcaacggcggcatcctgcagtacgtgct gcgcaacatactgaagtcaggcGGTTTGTCTGGTCAACC ACCGCGGTCTCAGTGGTGTACGGTACAAACC tgaccgagcgcccgtgcccaaggtcagcgaggaccatctggcggctc gccgccgtcagatcctcgacggt | 33 |
| Rv1488 | Rv1488 | cggtgaggtcaaaccactcatcggaccactctattgagtcaacctgggg ggcgtccccagGGTTTGTACCGTACACCACTGAG ACCGCGGTGGTTGACCAGACAAACCaaacacca gaccagcaacggctccttgcaccggaattcctttctcgagtccctacacgt c | 34 |
| Rv1543 | Rv1543 | tgattgttcggtttcggaaggctcatggtgtcaccaatggatccctcgggt ggcccgcacGGTTTGTACCGTACACCACTGAGAC CGCGGTGGTTGACCAGACAAACCgacgaagttcgtt aagtcaccaagattcatcgtgggtagctcctgatggcggcgtgggt | 35 |
| Rv1592c | Rv1592c | atcacgcgcgaggatgccggatggccatgaagggagcctaatggtaga gcccggcaatttggcaggcgcgGGTTTGTCTGGTCAACC ACCGCGGTCTCAGTGGTGTACGGTACAAACC ggcaggaagttgagccgccgtccgctctgacctggccaatgcgctctgc gcataccggcgcgaactcgga | 36 |

TABLE 5-continued

Examples of targeting oligonucleotides

| Oligo Name | | Sequence | SEQ ID NO: |
|---|---|---|---|
| Rv1620c-1623c | cyd operon | tcggccccgtagtatctccggagatgacagatgaatgtcgtcgacatttc gcggtggcagGGTTTGTCTGGTCAACCACCGCGG TCTCAGTGGTGTACGGTACAAACCaacaacaccaa cgccagcgcaaagacctgagtcatcgatatcagcacgtaacgccgctca | 37 |
| Rv1621c | CydD | gcggcgctgcgccgctatctactcagcacggtggcctgcggggtcggg atctccggctgcGGTTTGTCTGGTCAACCACCGCG GTCTCAGTGGTGTACGGTACAAACCgaagtgaac tcggatggtttccgacgatgaaccgaccgagtgctgtgagtcgccgcca gc | 38 |
| Rv1623c | CydA | tcggccccgtagtatctccggagatgacagatgaatgtcgtcgacatttc gcggtggcagGGTTTGTCTGGTCAACCACCGCGG TCTCAGTGGTGTACGGTACAAACCgaggtagcac cattgtcgtttgcttactgaggccaactgaccccggaaaggagcagccg g | 39 |
| Rv1743 | pknE | cgcgcaccgctgcggacatgctgcgagagcaagcggaattgtccggg acgaggccacaccaccccgcgctaGGTTTGTACCGTACAC CACTGAGACCGCGGTGGTTGACCAGACAAA CCcccgatcagcctcgcgagccagctcggatcctgatagttcacgacc atgctgccgtcccacacgaacggc | 40 |
| Rv1747 | Rv1747 | ttccacctgggttgggcagtgaactgccgcctagcacgccttgaggcga atcttccagcgGGTTTGTACCGTACACCACTGAGA CCGCGGTGGTTGACCAGACAAACCgggcggggc ggctggttggctcatcggcaccaactgtatcgggaccgcagccgacgc cgg | 41 |
| Rv1901 | cinA | acggtcctacgttagttcatgcgtaggctcatggcggtgagcgcacgtgc gggcatcgtgGGTTTGTCTGGTCAACCACCGCGG TCTCAGTGGTGTACGGTACAAACCaccctgagcg gtatcccgggctcaccctagcgacggcgaaatcgacagcagcgcgac aaa | 42 |
| Rv2047 | Rv2047 | cccgtcacaagctgacacgacgaactaggttcagcgactgagatcgctt cccggaagcgcGGTTTGTACCGTACACCACTGAG ACCGCGGTGGTTGACCAGACAAACCtccgctggc cccggtgacggcgattctcacggtcctactcgtcgtcgttccgaaacgcc g | 43 |
| Rv2048c | Pks12 | ggctgaagtgtcttgcggtgatgagccgagcagttctcgacgcatatagc cggccagcgcGGTTTGTACCGTACACCACTGAGA CCGCGGTGGTTGACCAGACAAACCcccggccaga tcccacccacggtcggtgggaaattctgacatcacgtccctggcgtcgg c | 44 |
| Rv2241 | aceE | cgcccgccagtaccggatcgacgacgtggcggctgcgcccgagcaga ccacggatcccggtcccggggccGGTTTGTCTGGTCAAC CACCGCGGTCTCAGTGGTGTACGGTACAAAC Ctaacgccggcgagccgaccgcctttggccgaatcttccagaaatctgg cgtagcttttaggagtgaacga | 45 |
| Rv2383c | mbtB | agcccgacgatgacgaccggggtcgttatcggacatcggcactcaccatc cgggccacggcgtcgaggtgaGGTTTGTACCGTACACC ACTGAGACCGCGGTGGTTGACCAGACAAAC Ccgaatgatctccgagcacgccgtagcatgcaccacaaaccctcccct gttagcacaggctgccctaattt | 46 |
| Rv2384 | mbtA | acctgcgctaccagccccctgttaaggagcccacatgccaccgaagg cggcagatggccgccgaccccagGGTTTGTCTGGTCAAC CACCGCGGTCTCAGTGGTGTACGGTACAAAC Ccgacgggtcccgtgacgacccagcgctgccattgactgacgtcaaca agttgaattgactgcgttgcatg | 47 |
| Rv2398c | cysW | gaagtcgccgtagcgtttggtggcgtcggccacgacgatggcgtaggtc atttttcaccgtctccttctcaGGTTTGTACCGTACACCAC TGAGACCGCGGTGGTTGACCAGACAAACCgc cctcgctgaccgctcgtgcccggcgggcgtctagcaccatctggacgat cagcaccaccacggaaacc | 48 |

TABLE 5-continued

Examples of targeting oligonucleotides

| Oligo Name | | Sequence | SEQ ID NO: |
|---|---|---|---|
| Rv2563 | Rv2563 | tcatttgattgggtccacggaagcaggtagcttccgtcgcatgcttttttgcg gctttgcgtgatgtccaaGGTTTGTCTGGTCAACCACC GCGGTCTCAGTGGTGTACGGTACAAACCattga gcaccgcgagcttgccagcgaatagttcggcaccaagtcgcgatccctg agggttgcgatgggcg | 49 |
| Rv2564 | Rv2564 | tcatttgattgggtccacggaagcaggtagcttccgtcgcatgcttttttgcg gctttgcgtgatgtccaaGGTTTGTCTGGTCAACCACC GCGGTCTCAGTGGTGTACGGTACAAACCattga gcaccgcgagcttgccagcgaatagttcggcaccaagtcgcgatccctg agggttgcgatgggcg | 50 |
| Rv2684 | arsA | tgcttgctgcggcactgaagacttgacctcgtgagcgtcgtcgcggtcac catcttcgtgGGTTTGTCTGGTCAACCACCGCGGT CTCAGTGGTGTACGGTACAAACCtggttgcggtactt cgtgttgttgcactgaccatctgtattgccgacagacctgtagcac | 51 |
| Rv2746c | pgsA3 | aaactccttgtccacctcgcaatcgtcatcaggtgaacgccgccggcggt ggggttggttcccgcaatcaGGTTTGTACCGTACACCA CTGAGACCGCGGTGGTTGACCAGACAAACCg ctggcggtctggcggatcccccgatgtcccgcagagccctggccacg taatcgacaccagtgatcacg | 52 |
| Rv2868c | gcpE | cggagccgacatctgcgaactcccttggtgggaactgacggccactga atgaaaagctgaccctatcaGGTTTGTACCGTACACCA CTGAGACCGCGGTGGTTGACCAGACAAACCg cttacggtcacaataggcgaaccgctcggtgtcgcgcccggatcttgctc gcccatttcggcggccagc | 53 |
| Rv2977c | thiL | cgctcgacgagctcactcaacggccgtgcggtcactgcatcccctttcgc gtacagacggtcaccgcgtcaGGTTTGTACCGTACACC ACTGAGACCGCGGTGGTTGACCAGACAAAC Cccctagcgaaccttgattgtctggctccccaaacgattgccagcccgc gtatccagtccactcctcgccg | 54 |
| RV2986c | hupB | gcgggcctaacacacggataccttcgtcacattgccaccgtgcaaagg gtatccgtgtgtcttgacctaGGTTTGTACCGTACACCAC TGAGACCGCGGTGGTTGACCAGACAAACCttt gcgaccccgccgagcggttgccttcttggcgggagccttggtagccgg ccgcttggccgctgccttc | 55 |
| Rv3034c | Rv3034c | ggcagccaatttcgcgtacccgatgtggatggtcgccggagcaccatcg gctttagggtgctcggggctaGGTTTGTACCGTACACCA CTGAGACCGCGGTGGTTGACCAGACAAACCg cgggccgccttcttgcgttcgatgtcggccaaggcagcggctagctcag cgcgctgcgcggccgatgcc | 56 |
| Rv3136 | PPE51 | atccgcacaaatgtaaggagctgagacacaatggatttcgcactgttacc accggaagtcGGTTTGTCTGGTCAACCACCGCGG TCTCAGTGGTGTACGGTACAAACCgtgatggccca cccacccgcggcagggtaacccggcgcctaaccgacaggcggcccgt tg | 57 |
| Rv3206c | moeB1 | ggcggctcgacattcacaccggtcagcctagtagagcccatcgggtgt attgggcctgtatcggtcctaGGTTTGTACCGTACACCA CTGAGACCGCGGTGGTTGACCAGACAAACCg tacatcaccatgtcgggctgcatctgcttggcccacgcgacgatcccacc ctgcaggtgtaccgcgtcg | 58 |
| Rv3211 | rhlE | acacgaccgacaccgtcaccgaaaggccgcttaccctcgtatgaccgc agtgaaacacacaactgaatcaGGTTTGTCTGGTCAACC ACCGCGGTCTCAGTGGTGTACGGTACAAACC caggacggcttcgccgcgcgggctaactgacccgcccaccgcatggtt aaaccggagcgccgcaccaaga | 59 |
| Rv3212 | Rv3212 | agcagtgatcccggcagtttctggatccagggtcattgagcaacgtggc gacacactagtcgctctgggtGGTTTGTCTGGTCAACCA CCGCGGTCTCAGTGGTGTACGGTACAAACCt gatcgcctatgttggcgcgagcagacgcaaaatcgcccgaaaccgatg gctttcgggcgattttgcgtc | 60 |

TABLE 5-continued

Examples of targeting oligonucleotides

| Oligo Name | | Sequence | SEQ ID NO: |
|---|---|---|---|
| Rv3270 | ctpC | atcagcgacctgcacgaccacgaccactgagcgcctcgccatgaccct ggaagtggtatcggacgcggccGGTTTGTCTGGTCAACC ACCGCGGTCTCAGTGGTGTACGGTACAAACC cggttgatccgctaccgcctggaccgctagcagccgcagccgtgacca cgccaggtgcggatgccctgcc | 61 |
| Rv3283 | sseA | cttcggactgggccaggtcgccagcggtaggctcgatgatgtgccgctt cccgcagaccctagccccaccGGTTTGTCTGGTCAACC ACCGCGGTCTCAGTGGTGTACGGTACAAACC gaagaaccaggagtggtacccgtcgtatgaccgcgcccgcgagcctgc ccgcgccgctagcagaggtggt | 62 |
| Rv3296 | lhr | gtaggcggttttttgtcggtgcctgttggcacgatggctaggtgaggttcgc gcagccttcagcactgagcGGTTTGTCTGGTCAACCAC CGCGGTCTCAGTGGTGTACGGTACAAACCcgc acacctcgcggtctgcggcggcggtaagccatgcccgagggcgacac cgtctggcacaccgcggcca | 63 |
| Rv3370c | dnaE2 | gccagagtgaaatccacgacgcgtttgcggcgtgtcgcgtcgcccgttt cactgtcggcgcagaggttcaGGTTTGTACCGTACACCA CTGAGACCGCGGTGGTTGACCAGACAAACCc cggaagtcgcgcgagcgcgcgccgaccgccagggtgaggcggccca tccgttcggcgacgacggtgatt | 64 |
| Rv3410c | guaB3 | atccggcttcatcgctgcagtatgaccccctttacatcgggccagttaatc agtctctcaggtggcgtcaGGTTTGTACCGTACACCAC TGAGACCGCGGTGGTTGACCAGACAAACCgc ccccaacggtcaggccgaccttctggaactccttgaggtcgcaatacc ggccttggccatcgatcgg | 65 |
| Rv3441c | mrsA | tttacgctatcgggtctcatgcctattcggacgccccgcgccgcgtcggg gttccagcattttccggttcaGGTTTGTACCGTACACCAC TGAGACCGCGGTGGTTGACCAGACAAACCgc gcgcggtgctcaccgcgtcggcgaccgtggccgccagccgctgggcg acgccctcgtcggctgcctcc | 66 |
| Rv3465 | rmlC | tgtgcgcgcgtctggcctgctgcccaggtgggaacagacgcagcggtt cattggggagatgcgcggcaccGGTTTGTCTGGTCAACC ACCGCGGTCTCAGTGGTGTACGGTACAAACC tagctcggtaatcccttgtgttgctttagcttcagcggtcacagcgcggcg attgttgtcggtggcccct | 67 |
| Rv3544c | fadE28 | ccgtatctcggcttgcagctggcgctgctccggcgtcaggtcaatgaaca tcgcgctcccaggagctcaaGGTTTGTACCGTACACCA CTGAGACCGCGGTGGTTGACCAGACAAACCa cggcttgctgttccgcagtgggatcgaaatccattagtgagcaaccggg catctaccggtgtagtcgac | 68 |
| Rv3574 | kstR | gcgctcccgacgcaccacctcgcgcggtcatgaaagtggcggtacttg ccgagtccgagctcggatcggaGGTTTGTCTGGTCAACC ACCGCGGTCTCAGTGGTGTACGGTACAAACC tgcggctgctgatcggcgatcaagacagcgcctagaagacttacgccg gcggacccgcggtgcggcccg | 69 |
| Rv3581c | ispF | cacgacgtgccagcttacctgcccaattgctgcaacctgcggcgcgcgc gtccggaccaggagtgcgctaGGTTTGTACCGTACACC ACTGAGACCGCGGTGGTTGACCAGACAAAC Cccgcaacgaaaccaccaatgccgtagcgattgcggccaagccctcg ccgcggccagtgaggcccagcccg | 70 |
| Rv3663c | dppD | tcgcgcacccggtcgctggccgcagcaacgcccgggagctccattagc ggagccagcgggtcgaccgtcaGGTTTGTACCGTACAC CACTGAGACCGCGGTGGTTGACCAGACAAA CCcaggttgccaacctttcggggagctgagggggcaccgggaatggc ctgaagcaactggcgggtgtactcg | 71 |
| Rv3680 | Rv3680 | ctcggaatcacttgcccagcagggggttcgatgagtgtcacaccgaaga ccctcgatatgGGTTTGTCTGGTCAACCACCGCGG TCTCAGTGGTGTACGGTACAAACCaacgatgcgg gccgcgcagcgggccgctgaggaaccggcccatcagtgacggtcgg caac | 72 |

TABLE 5-continued

Examples of targeting oligonucleotides

| Oligo Name | | Sequence | SEQ ID NO: |
|---|---|---|---|
| Rv3696 | glpK | cgagcgtgcggacatgttcaggcgcacagcgaaagctaggacacgtca acccaatccagggtccgctgcaGGTTTGTACCGTACACC ACTGAGACCGCGGTGGTTGACCAGACAAAC Ctcggccaattgctctcctaggatggcgtcggacactgcatgtaatcgtc catgatggtccaccgcagcgg | 73 |
| Rv3822 | Rv3822 | cggcgggcttgcctaacgcagagctctcacatgaaatgtccaggcgtct ccgactgcgttGGTTTGTCTGGTCAACCACCGCGG TCTCAGTGGTGTACGGTACAAACCggtttgctaccc aaagggaagaagcactagccataaagtccacgacctacggtggcgttt | 74 |
| Rv3848 | Rv3848 | cgtcgacaacgcgtcgaaaggtcgcctgccatgctcgccgccacactg ctaagtctgggaGGTTTGTCTGGTCAACCACCGCG GTCTCAGTGGTGTACGGTACAAACCggccgcatc cgcccgacacggtcatcctgatctgctcgccgaacacgtgggcgacgg acc | 75 |
| Rv3869 | EccB1 | cgccgcggtgcacgcacacctcaacatgagagaatgaactatgggcgctt cgcctcaccaccaaggttcagGGTTTGTCTGGTCAACCA CCGCGGTCTCAGTGGTGTACGGTACAAACCg ttcccgccggagcctccggagcccccctgatgacgaccaagaagttcact cccaccattacccgtggccc | 76 |
| Rv3910 | Rv3910 | cacggccggacagtaaccaatcggtggcggcatagcacttcaccctgg ctggccgtgcccggcccggtcaGGTTTGTACCGTACACC ACTGAGACCGCGGTGGTTGACCAGACAAAC Cggacgcggcgtaaatcgtgatctccgagatgtcggcttgactattccg tcggtggttcccaaggtagag | 77 |
| Nar operon | Nar operon | gaatggcacgacggtgattgtggcagagaactaccacccacgacgacg cggcgcggaaccGGTTTGTACCGTACACCACTGAG ACCGCGGTGGTTGACCAGACAAACCggtccacc gacgtgaggtgtaacggtcacgggatgaccctcctcgtcatgagcggtg tgg | 78 |

What is claimed is:

1. A method for genetic modification of a bacterium, the method comprising contacting a bacterium with:
   (i) a single-stranded targeting oligonucleotide comprising an attP attachment site flanked by homology arms that are homologous to a target nucleic acid sequence of the bacterium; and,
   (ii) a non-replicating payload plasmid comprising an attB attachment site and a nucleic acid sequence encoding a selectable marker,
   wherein a single strand annealing protein (SSAP) and/or an integrase protein is expressed in the bacterium.

2. The method of claim 1, wherein the bacterium is a *Mycobacterium*.

3. The method of claim 1, wherein each homology arm comprises a nucleic acid sequence that is between 25 and 100 bases long.

4. The method of claim 1, wherein the single-stranded targeting oligonucleotide comprises a sequence selected from SEQ ID NOs: 12 to 78.

5. The method of claim 1, wherein the attP attachment site is a Bxb1 attP attachment site.

6. The method of claim 1, wherein the attB attachment site is a Bxb1 attB attachment site.

7. The method of claim 1, wherein the selectable marker comprises a nucleic acid sequence encoding a drug resistance gene.

8. The method of claim 1, wherein the non-replicating payload plasmid further comprises a nucleic acid sequence encoding a promoter sequence or a peptide.

9. The method of claim 1, wherein the integrase protein expressed in the bacterium is Bxb1 phage integrase.

10. The method of claim 1, wherein the SSAP expressed in the bacterium is a RecT protein.

11. The method of claim 1, wherein the bacterium is contacted simultaneously with the single-stranded targeting oligonucleotide and the non-replicating payload plasmid.

12. The method of claim 8, wherein the contacting results in a deletion of the target nucleic acid sequence or an insertion of the nucleic acid sequence encoding the promoter sequence or the peptide into the genome of the bacterium.

13. A bacterial cell comprising:
   (i) a single-stranded targeting oligonucleotide comprising an attP attachment site flanked by homology arms that are homologous to a target nucleic acid sequence of the bacterial cell; and,
   (ii) a non-replicating payload plasmid comprising an attB attachment site and a nucleic acid sequence encoding a selectable marker,
   wherein a single strand annealing protein (SSAP) and/or an integrase protein is expressed in the bacterial cell.

14. The bacterial cell of claim 13, wherein the bacterial cell is a *Mycobacterium* cell.

15. The bacterial cell of claim 13, wherein the cell comprises a plasmid encoding the SSAP and/or the integrase protein.

16. The bacterial cell of claim 13, wherein the targeting oligonucleotide comprises a sequence selected from SEQ ID NOs: 12 to 78.

17. The bacterial cell of claim 13, wherein the non-replicating payload plasmid further comprises a nucleic acid sequence encoding a promoter sequence or a peptide.

18. The bacterial cell of claim 13, wherein the integrase protein expressed in the bacterial cell is Bxb1 phage integrase.

19. The bacterial cell of claim 13, wherein the SSAP expressed in the bacterial cell is a RecT protein.

* * * * *